(12) United States Patent
Henschel et al.

(10) Patent No.: US 11,229,797 B2
(45) Date of Patent: Jan. 25, 2022

(54) TWO-POLE ELECTRIC CONTACT CONNECTOR FOR IMPLANTABLE MEDICAL DEVICE COMPONENTS

(71) Applicant: BIOTRONIK SE & Co. KG, Berlin (DE)

(72) Inventors: Martin Henschel, Berlin (DE); Kathy Hartmann-Bax, Nuthe-Urstromtal (DE); Torsten Oertmann, Blankenfelde (DE)

(73) Assignee: BIOTRONIK SE & CO. KG

( * ) Notice: Subject to any disclaimer, the term of this patent is extended or adjusted under 35 U.S.C. 154(b) by 57 days.

(21) Appl. No.: 16/775,498

(22) Filed: Jan. 29, 2020

(65) Prior Publication Data
US 2020/0238092 A1   Jul. 30, 2020

(30) Foreign Application Priority Data

Jan. 30, 2019 (EP) .................................... 19154499
Aug. 19, 2019 (EP) .................................... 19192352

(51) Int. Cl.
*A61N 1/375* (2006.01)
*A61N 1/378* (2006.01)
*H01M 50/502* (2021.01)

(52) U.S. Cl.
CPC ........... *A61N 1/3754* (2013.01); *A61N 1/378* (2013.01); *H01M 50/502* (2021.01)

(58) Field of Classification Search
None
See application file for complete search history.

(56) References Cited

U.S. PATENT DOCUMENTS

| | | | |
|---|---|---|---|
| 4,743,205 A | 5/1988 | Mitani et al. | |
| 4,827,378 A * | 5/1989 | Gillan | H01R 24/50 174/382 |
| 5,103,818 A | 4/1992 | Maston et al. | |
| 5,791,911 A | 8/1998 | Fasano et al. | |
| 6,079,986 A * | 6/2000 | Beshears | H01R 24/50 439/63 |
| 6,086,383 A * | 7/2000 | Fasano | H01R 12/57 439/63 |
| 7,118,383 B2 * | 10/2006 | Nagata | H01R 13/6315 439/63 |
| 9,136,639 B2 * | 9/2015 | Loureiro | H01R 13/527 |

(Continued)

OTHER PUBLICATIONS

European Search Report, dated Mar. 5, 2020, Appln. No. 19192352.3-1210.

*Primary Examiner* — Brian T Gedeon
(74) *Attorney, Agent, or Firm* — Craig A. Fieschko, Esq.; DeWitt LLP

(57) ABSTRACT

A connector arrangement (3) for establishing a two-pole electric contact between components of an implantable medical device (4) includes: a first connector portion (1) including a first contact element (11) and a pin receptacle (12); and a second connector portion (2) including a second contact element (21) and a contact pin (22). The connector arrangement (3) is configured to assume a connected state wherein the first contact element (11) is in contact with the second contact element (21) and the contact pin (22) is received in the pin receptacle (12). At least a part of the first connector portion (1) and/or at least a part of the second connector portion (2) is mounted on a printed circuit board (41).

20 Claims, 16 Drawing Sheets

(56) References Cited

U.S. PATENT DOCUMENTS

| | | | |
|---|---|---|---|
| 2002/0139574 A1* | 10/2002 | Hosaka | H05K 3/3426 |
| | | | 174/256 |
| 2005/0026498 A1* | 2/2005 | Ikeda | H01R 13/6277 |
| | | | 439/582 |
| 2007/0150020 A1 | 6/2007 | Hokanson et al. | |
| 2011/0021071 A1* | 1/2011 | Chen | H01R 24/50 |
| | | | 439/578 |
| 2016/0315302 A1 | 10/2016 | Aamodt et al. | |

* cited by examiner

TWO-POLE ELECTRIC CONTACT CONNECTOR FOR IMPLANTABLE MEDICAL DEVICE COMPONENTS

FIELD OF THE INVENTION

The invention relates to a connector arrangement for establishing a two-pole electric contact between components of an implantable medical device, as well as an implantable medical device including such a connector arrangement.

BACKGROUND OF THE INVENTION

Nowadays, components of implantable medical devices are usually provided with adapters for enabling an electrical connection, e.g., between a battery or a capacitor and a functional component of an implantable medical device. In most cases, components such as a battery or a capacitor, have two potentials which need to be connected: a plus pole (cathode), which may be contacted, e.g., via a feedthrough pin, and a minus pole (anode), which may be contacted, e.g., via a further pin or an adapter, or directly at a housing of the battery or capacitor. Frequently, the housing has the minus potential. Conventionally, adapters are provided on the plus and/or minus pole, such that a two-pole electric contact with a functional component of the implantable medical device may be achieved by welding, soldering, or brazing on the adapters.

The document US 2016/0315302 A1 describes an implantable medical device including a battery housing, a feedthrough member extending from the battery housing, and a connector including at least one electrical terminal electrically communicating with the feedthrough member.

The document US 2007/0150020 A1 describes a battery for use with implantable medical devices, the battery including a battery housing, a connector block connected to the battery housing, and a feedthrough assembly having a ferrule, wherein at least a portion of the ferrule extends outside the battery housing, and within the connector block.

It is a drawback of the known solutions that additional adapters need to be arranged on the components, such as on the battery, capacitor and/or the functional component of the implantable medical device. Such adapters require space and make the product more expensive. Currently, metallurgical connections (such as welding or soldering) are usually used for the electrical ground contact as well as for the anode contact. The soldering or welding locations require a relatively large amount of space on the circuit. Furthermore, such adapters may increase the number of contact transitions, yielding increased contact resistances and power losses. As a result, the lifetime of an implant may be shortened.

An exemplary known solution in connection with a battery of an implant functions as follows: a foil is welded on a battery pad. This is the adapter, which is welded on the housing of the battery. One end of a wiring strip is then welded to the adapter. The other end of the wiring strip is welded to a metallic pad, which in turn is soldered to circuitry of the implant. As a result, the following transitions are formed: battery housing—metal foil—battery adapter pad—wiring strip—circuitry adapter pad—circuitry. This amounts to 5 metallurgical transitions at the minus pole and 4 metallurgical transitions at the plus pole, i.e., 9 transitions in the closed electric circuit.

SUMMARY OF THE INVENTION

The present invention seeks to provide an improved connector arrangement for establishing a two-pole electric contact between components of an implantable medical device.

In an exemplary version, a connector arrangement for establishing a two-pole electric contact between components of an implantable medical device includes a first connector portion including a first contact element and a pin receptacle, and a second connector portion including a second contact element and a contact pin. The connector arrangement is configured to assume a connected state in which the first contact element is in contact with the second contact element and the contact pin is received in the pin receptacle. At least a part of the first connector portion and/or of the second connector portion is mounted on a printed circuit board (PCB). Preferably, the first contact element and the pin receptacle are mounted on the PCB.

The connector arrangement may be provided within an implantable medical device, wherein the PCB is a part of an electronics module of the implantable medical device.

These arrangements directly connect a connector portion with a PCB instead of using an additional adapter. With this solution, the number of contact transitions may be reduced, e.g., to two contact transitions for each pole. For example, in the connected state, the first contact element may be in contact with the second contact element to connect a first pole (e.g. the minus pole), and the contact pin may be received in the pin receptacle to connect a second pole (e.g. the plus pole). This arrangement can provide only two interconnection transitions at each pole: a transition from, e.g., a battery housing to the first contact element, and a transition from the first contact element to the circuitry (minus pole); and a transition from the contact pin to the first connector portion, and a transition from the first connector portion to the circuitry (plus pole). This yields 4 transitions for the closed electric circuit.

By reducing the number of required metallurgical transitions, the contact resistance and the corresponding power losses may be reduced. In addition, contact reliability may be enhanced, since fewer process steps are involved in the formation of the interconnection. A space reduction of the interconnection may also be achieved. For example, the required volume of the interconnections may be reduced by greater than 50% as compared to prior art solutions due to the fewer required welding contacts. Furthermore, processing costs may be saved due to a reduction of the processing time required for establishing the interconnections (fewer welding steps). More generally, product costs may be reduced by avoiding a dedicated battery adapter.

When the connector arrangement is provided in an implantable medical device, the first connector portion may be mounted on the PCB of the implantable medical device, and the second connector portion may be arranged on a battery, a capacitor, or a feedthrough assembly of the implantable medical device.

The first connector portion and/or the second connector portion may form at least a part of a surface-mount device (SMD) that is mounted on the PCB of the implantable medical device.

In other words, a surface-mount technology (SMT) may be used for attaching the first connector portion and/or the second connector portion to the PCB. Thus, automated assembly may be facilitated, e.g. by allowing for an automated placement of the first connector portion and/or the second connector portion on the PCB. For example, the first connector portion and/or the second connector portion, which is formed as SMD, may thus be automatically soldered to the PCB, e. g. in an automated reflow soldering process.

In an exemplary version, the pin receptacle is mounted on a first side of the PCB, whereas the first contact element is mounted on a second side of the PCB opposite the first side of the PCB. Each of the pin receptacle and the first contact element may be soldered to the PCB sequentially by means of a respective reflow soldering process, that is, a top side and a bottom side of the PCB may be sequentially fitted with the pin receptacle and the first contact element, respectively.

The first connector portion may include a contact pad. The pin receptacle may be formed in the contact pad, e.g., as a hole extending into or through the contact pad.

The first connector portion may include at least one guidance element that is configured to align the first contact element and the contact pad. In particular, the guidance element may be configured to axially align the first contact element and the contact pad during assembly, e.g., during a reflow soldering process. For example, during the soldering process, when each of the pin receptacle and the first contact element "swim" in the solder for a short while and the solder solidifies while cooling, there is a risk that an axial offset may arise between these two contact components. This offset may be partially compensated for by means of inclined insertion surfaces that may be provided at the contact pin and/or at the pad which includes the pin receptacle, such that the contact pin is guided towards the hole (i.e., the pin receptacle) formed in the contact pad. To further minimize such position tolerances, one or more guidance elements may be arranged at the first contact element and/or at the contact pad so as to ensure an axial alignment by avoiding an unwanted displacement during the reflow process (i.e., while the solder is liquid).

When the connector arrangement is in the connected state, the contact pin may be materially bonded with the pin receptacle. The material bond may be a metallurgical bond, such as a welded joint, a soldered joint, or a brazed joint. Fixing the contact pin to the pin receptacle (e.g., to a contact pad forming the pin receptacle) by means of welding or soldering may better ensure the high contact reliability required for medical implants. Further, by welding, soldering, or otherwise fixing the contact pin to the pin receptacle, the first contact element is held in contact with the second contact element. A spring connection or a latching connection (also referred to as snap-in connection) may be provided between the first contact element and the second contact element, wherein the welding, soldering, or otherwise fixing of the connection pin and the pin receptacle may secure the spring connection or latching connection of the first contact element and the second contact element. Thus, the welding joint or soldering joint may secure the connection at both electric poles (plus and minus) at the same time. Further, the pin contact and/or the mechanical contact (e.g., spring contact and/or latching contact) between the first contact element and the second contact element may also facilitate the welding and/or soldering process by positioning the welding or soldering locations relative to each other without requiring a dedicated external tool (in accordance with the so-called "hands-off" principle during assembly).

In addition, automated placement and automated contacting of the components of the implantable medical device may be enabled with this connector assembly due to the uniaxial assembly.

Instead of (or in addition to) the aforementioned welding spots and/or soldering spots, further reliable contacts, such as a crimped contact, an installation displacement contact, and/or a spring contact, may be used. More generally, in addition to or instead of the above-mentioned material bond, the contact pin may be form-fittingly and/or force-fittingly connected to the pin receptacle in the connected state of the connector arrangement. In a preferred version the first connector portion includes a first spring element configured to establish a form-fitting and/or force-fitting connection between the pin receptacle and the contact pin in the connected state of the connector arrangement.

In an exemplary version, the first contact element and the second contact element are configured to be connected with each other by means of a spring connection and/or by means of a snap-in connection (i.e., a latching connection) in the connected state of the connector arrangement. For example, one of the first contact element and the second contact element may include at least one second spring element and the other one of the first contact element and the second contact element may include at least one groove, wherein each second spring element engages with a corresponding groove in the connected state of the connector arrangement.

The first contact element and/or the second contact element may have an annular shape. For example, the first contact element may be formed in one piece having an annular shape. Alternatively, the first contact element may consist of several pieces, such as two basically semicircular elements.

In the connected state, the first contact element, the second contact element, the contact pin, and the pin receptacle may be arranged coaxially. In particular, each of the first contact element, the second contact element, the contact pin, and the pin receptacle may be arranged coaxially about a common axis. For example, the common axis may be defined by the longitudinal axis of the contact pin, the axis of the annulus of the first contact element, and the axis of the annulus of the second contact element. This coaxial arrangement may allow the connector arrangement to be very volume efficient (i.e., space-saving). In particular, it may not be necessary to provide contacts that are arranged next to each other. This may also reduce production costs since less contacts need to be welded.

Further, a simple, uniaxial assembly may be achieved in combination with a self-clamping function via a spring connection between the first contact element and the second contact element, and/or by a spring connection between the contact pin and the pin receptacle. The form-fitting and/or force-fitting connections between the first contact element and the second contact element and/or between the connection pin and the pin receptacle may also provide an integrated hold-down and alignment function for a wedding or soldering process which safely connects the pin receptacle and the contact pin. Owing to this self-clamping function, it is not necessary to hold down the components manually or via dedicated external tools, thereby better enabling a hands-off process.

The first connector portion and/or the second connector portion may include an insulation element, which may be formed of or include a plastic material, such as an insulating mold compound. For example, the first connection element may be mounted on such an insulation element.

The invention can be also used to connect the circuit board to one or more feedthrough(s) of the device header, e.g., to transmit and receive electrical signals from the heart leads that are connected to the header, or to transmit and receive RF signals from an antenna that is positioned within the header.

All features and/or functions of the versions of the inventions described above, and in the discussion below, can be combined with each other unless explicitly stated otherwise.

Further potential features, advantages, and objectives of the invention may be more readily understood with reference to the following detailed description and the exemplary versions of the invention shown in the drawings.

DETAILED DESCRIPTION OF EXEMPLARY VERSIONS OF THE INVENTION

Figure 1:
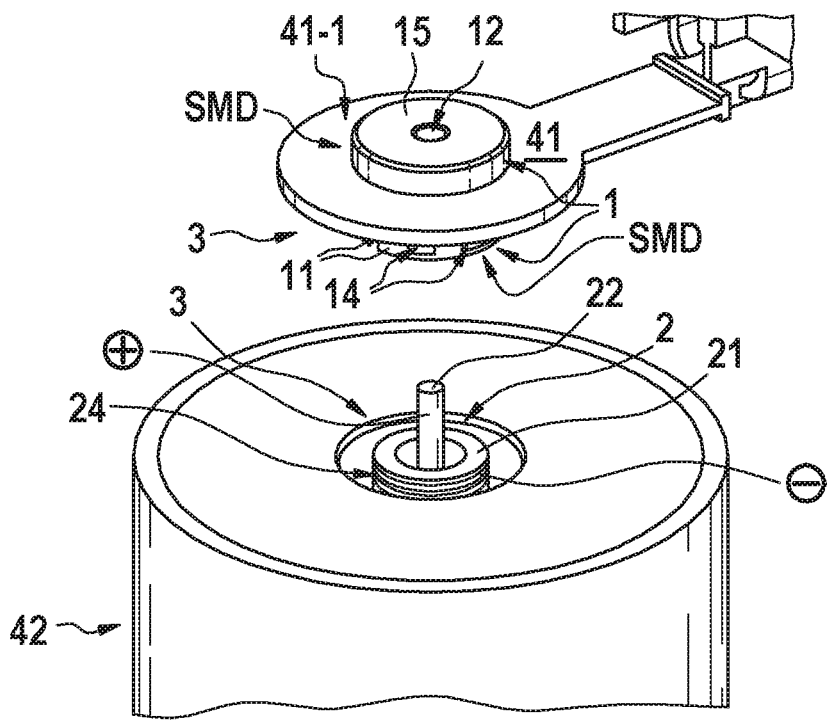
FIG. 1 shows a perspective view of a connector arrangement.

FIG. 1 shows a perspective view of an exemplary version of a connector arrangement 3. In this exemplary version, the connector arrangement 3 may establish a two-pole electric contact between a battery 42 of an implantable medical device and another component, such as an electronics module of the implantable medical device. The implantable medical device may be a pacemaker, an implantable cardioverter-defibrillator (ICD), a neurostimulator (e.g. for spinal cord stimulation), a loop recorder, a sensor (such as a pressure sensor), or a leadless pacemaker, among other devices.

The connector arrangement 3 includes a first connector portion 1 and a second connector portion 2. The first connector portion 1 includes a first contact element 11 and a pin receptacle 12. The first contact element 11 is a metallic element having an annular shape, such as a circular ring shape. The shape of the first contact element 11 will be explained in further detail below, e.g. with reference to FIGS. 7 and 8. The pin receptacle 12 is formed as a hole extending through a metallic contact pad 15 of the first connector portion 1.

The first connector portion 1 is mounted on a printed circuit board (PCB) 41. Specifically, the contact pad 15 including the pin receptacle 12 may be mounted in a first side (upper side) 41-1 of the PCB 41, and the first contact element 11 may be mounted on a second side (lower side) 41-2 (FIG. 2) of the PCB 41, wherein the second side 41-2 of the PCB 41 is opposite to the first site 41-1 of the PCB 41.

The PCB 41 may form a part of an electronics module of the implantable medical device. In other words, the PCB 41 of FIG. 1 may be only a portion of a larger PCB 41 of an electronics module of the implantable medical device. Thus, FIG. 1 might be regarded as depicting only a circular portion of the PCB 41 on which each of the first contact element 11 and the contact pad 15, which forms the pin receptacle 12, are mounted.

The contact pad 15, which includes the pin receptacle 12, is provided in the form of a surface-mount device (SMD) that is mounted on the first side 41-1 of the PCB 41. The first contact element 11 is also a part of an SMD, which is mounted on the second side 41-2 (FIG. 2) of the PCB 41. This will be explained in further detail below, e.g., with reference to FIGS. 2-4.

The second connector portion 2 includes a second contact element 21 and a contact pin 22, which are arranged on the battery 42. The contact pin 22 axially protrudes from a housing of the battery 42 and has a positive potential (+). In other words, the contact pin 22 forms a first pole (+) of the battery 42. The contact pin 22 may also extend into the interior of the battery 42, as seen in the cross-sectional view in FIG. 2. The second contact element 21 is provided in the form of a circular metallic element which extends around the contact pin 22 inside a recess formed in the battery housing. The second contact element 21 has a negative potential, thus forming a second pole (−) of the battery 24.

While the connector arrangement 3 is depicted in a disconnected state in FIG. 1, it is configured to assume a connected state in which the first contact element 11 is in contact with the second contact element 21 to connect the first pole (+), and the contact pin 22 is received in (and in contact with) the pin receptacle 12 to connect the second pole (−).

Figure 2:
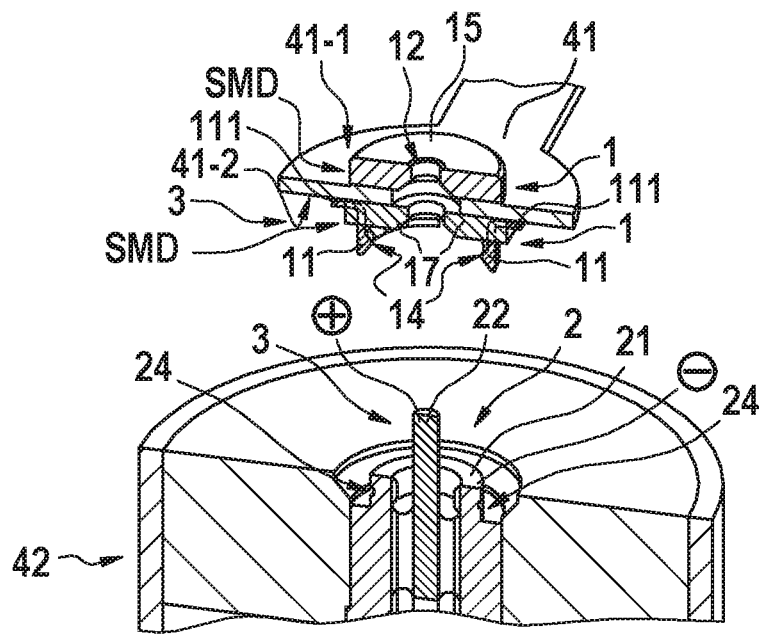
FIG. 2 shows a cross-sectional view of the connector arrangement of FIG. 1.

FIG. 2 shows a cross-sectional view of the connector arrangement 3 of FIG. 1, with the connector arrangement 3 still being in its disconnected state. In this cross-sectional view, further structural details regarding, e.g., the first connector portion 1, become apparent. For example, as illustrated in FIG. 2, the first connection element 11 may be mounted on an insulation element 17. The insulation element 17 may consist of an insulating mold compound or other plastic material. Thus, the insulation element 17 and the first connection element 11 may together form an SMD mounted on the second side 41-2 of the PCB 41. For establishing an electrical connection with the PCB 41, the SMD further includes bond feet 111, which are electrically connected with the first contact element 11. For example, the bond feet 111 may be formed in one (metallic) piece with the first contact element 11.

The cross-sectional view in FIG. 2 further reveals that the PCB 41 has a bore which is axially aligned with the pin receptacle 12 of the contact pad 15, so as to allow for the contact pin 22 to extend through the bore and into the pin receptacle 12 when the connector arrangement 3 is in the connected state.

Regarding further features of the first contact element 11, FIG. 2 illustrates several second spring elements 14, which laterally protrude from the ring-shaped first contact element 11. The second contact element 21 has a circumferential groove 24. When the connector arrangement 3 is in the connected state, the second spring elements 14 form-fittingly and force-fittingly engage with the groove 24 so as to secure a mechanical connection between the first contact element 11 and the second contact element 21. Hence, the first contact element 11 and the second contact and 21 are configured to be connected with each other by means of a spring connection or snap-in connection in the connected state.

Figure 3:
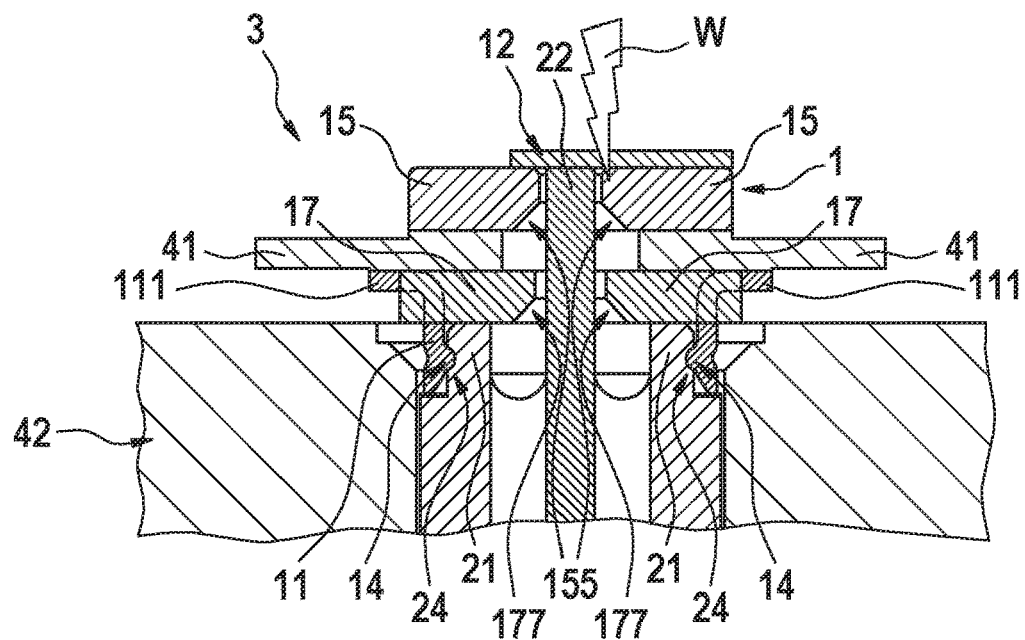
FIG. 3 shows a cross-sectional view of the connector arrangement of FIG. 1 in a connected state.

FIG. 3 shows a cross-sectional view of the connector arrangement 3 of FIGS. 1 and 2 in its connected state (also referred to as its mated condition). In the connected state, the contact pin 12 extends through the respective bores provided in the insulation element 17 and the PCB 41 into the pin receptacle 12. Thus, a contact is established between the contact pad 15 forming the pin receptacle 12 and the contact pin 22. The insulation element 17 and the contact pad 15 include inclined insertion surfaces 177, 155, which are configured to guide the contact pin 22 into the bore of the insulation element 17 and the pin receptacle 12. This allows a degree of compensation for any axial displacement between the insulation element 17, the PCB 41, and/or the contact pad 15.

Further, in the connected state, the first contact element 11 engages with the second contact element 21 so as to establish an electrical contact. Specifically, the second spring elements 14 engage with the groove 24 to secure the mechanical connection between the first contact element 11 and the second contact element 12, but also the connection between the first connector portion 1 and the second connector portion 2 as a whole.

In addition, in the connected state, the contact pin 22 may be materially bonded with the pin receptacle 12. Particularly, a metallurgical junction may be provided, e.g., by means of a welded joint, a soldered joint or a brazed joint. For example, the material junction may be created by means of a laser welding process W, as schematically indicated in FIG. 3. For example, by fixing the contact pin 22 to the pin receptacle 12 (i.e. to the contact pad 15 forming the pin receptacle 12) by means of welding or soldering, high contact reliability may be ensured, which is generally required for medical implants. Further, by welding. Soldering, or otherwise fixing the contact pin 22 to the pin receptacle 12, the first contact element 11 may be held in contact with the second contact element 21. Thus, the material bond between the contact pin 22 and the pin receptacle 12 may secure the connection between the first contact element 11 and the second contact element 21, in addition to the spring connection formed by the second spring elements 14 and the groove 24.

The connector assembly 3 of FIGS. 1-3, as well as all alternative versions of the connector assembly discussed below, directly connect the first connector portion 1 with the PCB 41 instead of via an additional adapter. This allows the number of contact transitions to be reduced to two contact transitions for each pole. Specifically, in the connected state, the first contact element 11 is in contact with the second contact element 21 to connect the first pole (−), and the contact pin 22 is be received in the pin receptacle 12 to connect the second pole (+). Only two interconnection transitions at each pole are sufficient: for the first pole (−), a transition from the second contact element 21 arranged on the battery housing to the first contact element 11, and a transition from the first contact element 11 to a pad on the PCB 41, which is connected to the functional circuitry of the implantable medical device; and for the second pole (+), a transition from the contact pin 22 to the contact pad 15 of the first connector portion 1, and a transition from the contact pad 15 to the circuitry (e. g. via a corresponding pad on the PCB 41). In sum, only four contact transitions are used for the closed electric circuit supplying the implantable medical device with energy.

Further, it should be noted that in the connected state as exemplified in FIG. 3, the first contact element 11, the second contact element 21, the contact pin 22, and the pin receptacle 12 may be arranged coaxially (about a common axis), e.g., about the central lengthwise axis of the contact pin 22, which also serves as the axis of the annular first contact element 11 and/or the second contact element 21. The connector arrangement 3 may be very volume-efficient (i.e., space-saving) due to such a coaxial arrangement of its components.

Figure 4:
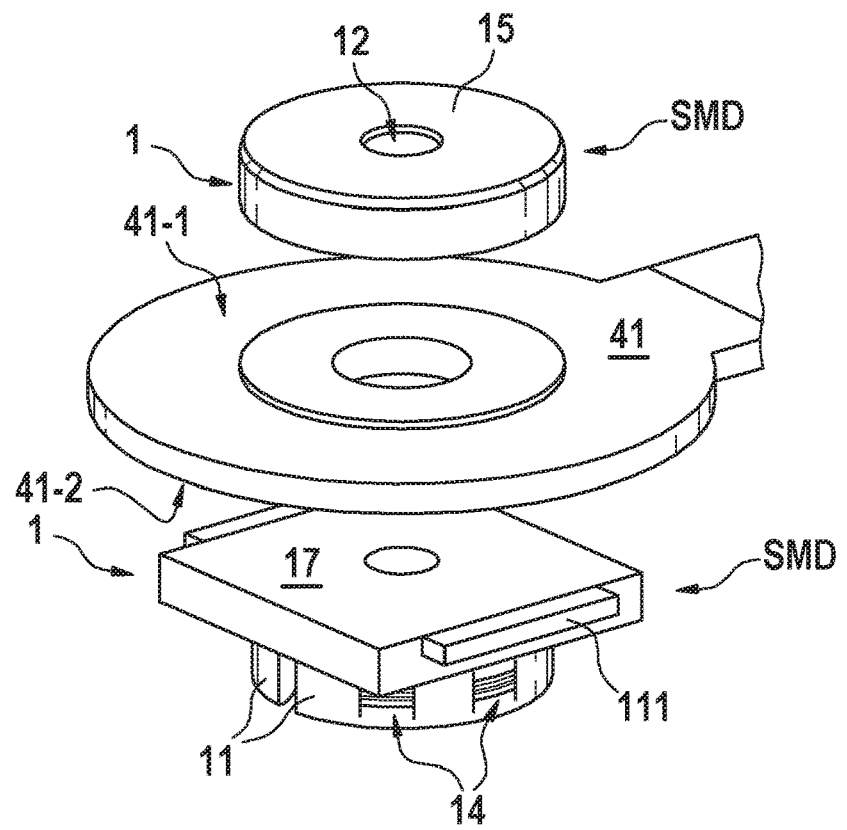
FIG. 4 shows an exploded view of a first connector portion of the connector arrangement of FIG. 1 in combination with a PCB.

FIG. 4 shows an exploded view of the first connector portion 1 of the connector arrangement 3 in combination with the PCB 41, showing the bore provided in the PCB 41 for allowing passage of the contact pin 12 in the connected state. FIG. 4 further illustrates the upper side of the insulation element 17, including the bond feet 111.

Figure 5:
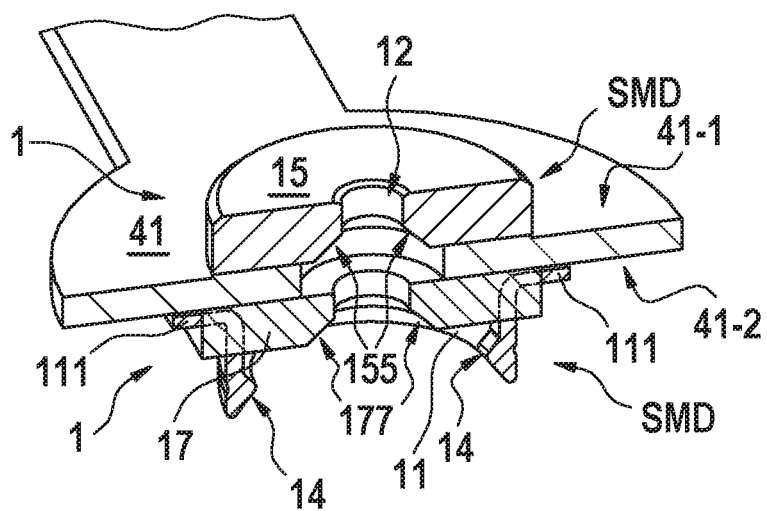
FIG. 5 shows a cross-sectional view of the first connector portion of FIG. 4 in an assembled state.

FIG. 5 shows a cross-sectional view of the first connector portion 1 of FIG. 4 in an assembled state, i.e., in a state wherein both surface-mount devices (the contact pad 15, as well as the insulation element 17 together with the first contact element 11) are coaxially mounted on respective sides of the PCB 41. The assembly of the SMDs may include reflow soldering steps in which the SMDs are attached to the PCB 4. The cross-sectional view of FIG. 5 also illustrates the inclined insertion surfaces 155, 177 mentioned above.

Figure 6:
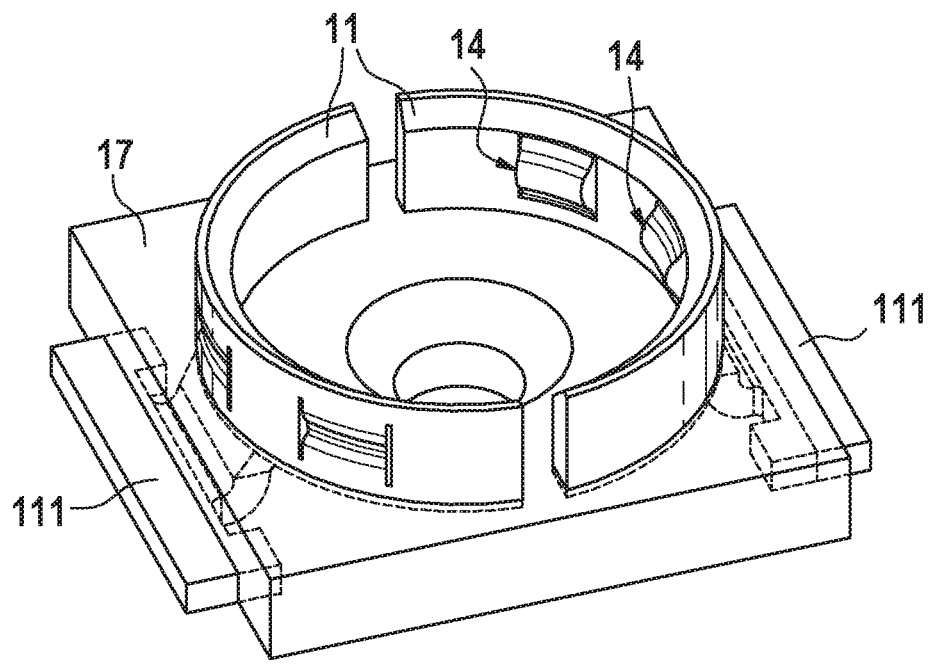
FIG. 6 shows a perspective view of a first contact element arranged on an insulation element.

FIG. 6 shows a perspective view of the first contact element 11 arranged on the insulation element 17. The metallic first contact element 11, including the second spring elements 14, may have a plating that includes at least one of phosphorus-bronze, nickel, and gold, though other conductive platings are also possible. Preferably, the first contact element 11 is provided with an electroless nickel inversion gold (ENIG) plating.

The insulation element 17 may include a molded plastic body, which may include or consist of one or more liquid-crystal polymers (LCP). The insulation element 17 may be partially molded about the first contact element 11.

Figure 7:
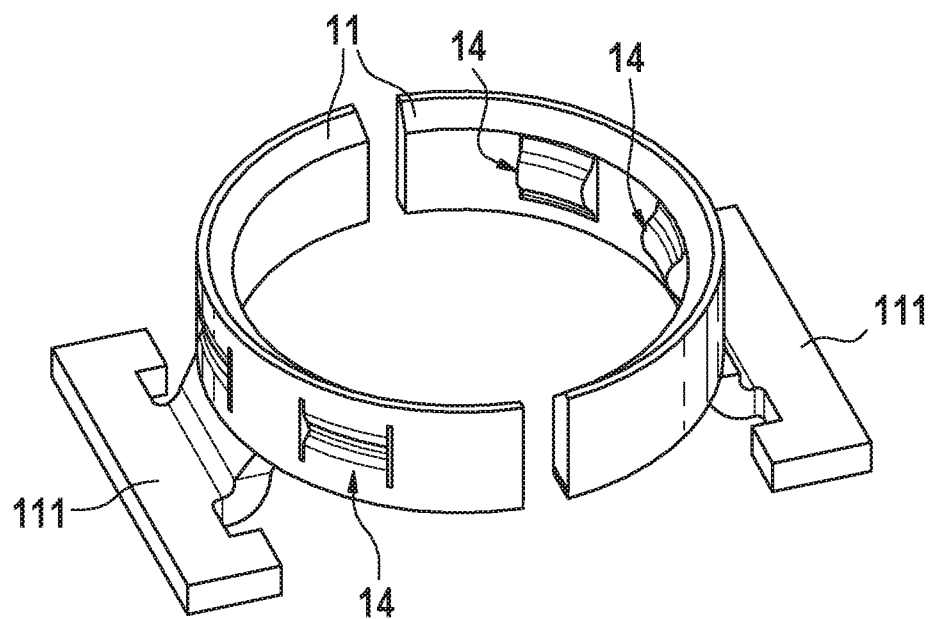
FIG. 7 shows a perspective view of the first contact element of FIG. 6.

FIG. 7 shows a perspective view of the first contact element 11 of FIG. 6. The first contact element 11 includes two separate basically semicircular elements, wherein each of these elements is formed as a single piece with a respective bond foot 111.

Figure 8:
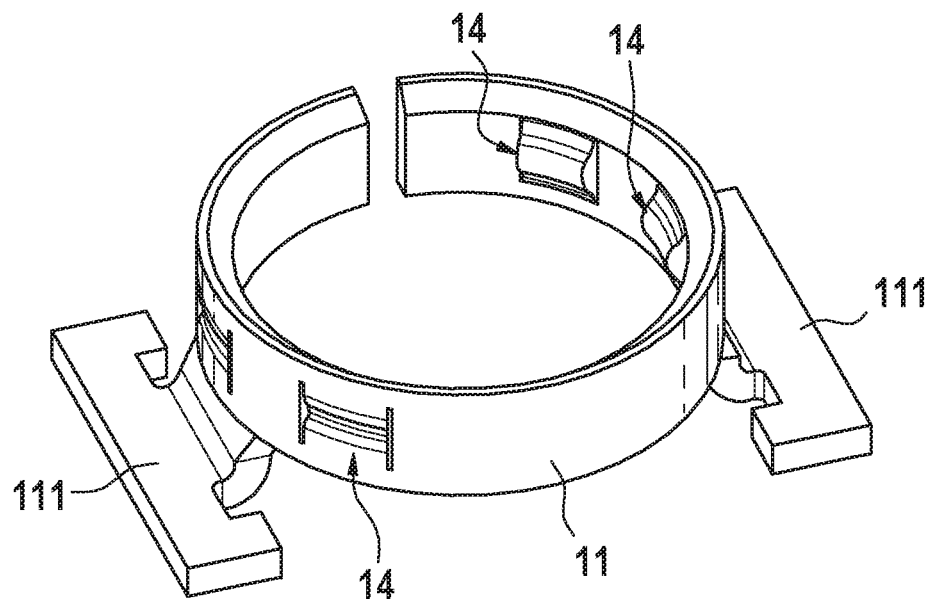
FIG. 8 shows a perspective view of another version of a first contact element.

FIG. 8 shows a perspective view of another exemplary version of the first (female) contact element 11. Here the first contact element 11, including the second spring elements 14, is formed as a single piece, which also includes two solderable bond feet 111. The bond feet 111 are provided for soldering or otherwise affixing the first contact element 11 to the PCB 41.

Figure 9:
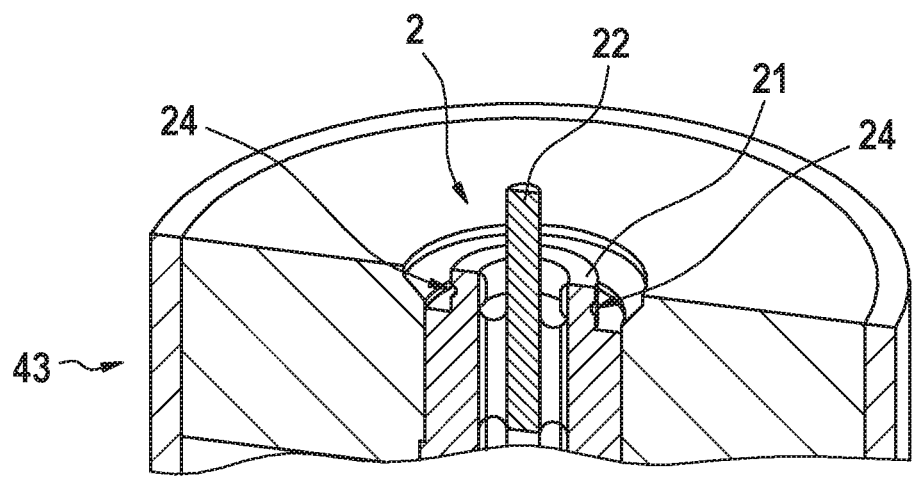
FIG. 9 shows a cross-sectional view of a feedthrough assembly having a second connector portion.

In another exemplary version shown in FIG. 9, a second connector portion 2 is provided on a feedthrough assembly 43, instead of on the battery 42 as in FIGS. 1-3. The term "feedthrough" here refers to a component that hermetically seals about a conductive pin extending from the inner assembly of the battery, and which transmits electrical energy to the device electronics. The second contact element 21, which may be plated with gold or another suitable plating material, is provided inside a recess formed in the housing of the feedthrough assembly 43, similar to the arrangement described above with respect to FIGS. 1 and 2. As a result, the second contact element 21 does not extend beyond an outer envelope of the housing of the feedthrough assembly 42, providing a very volume-efficient (i.e., space-saving) design.

Figure 10:
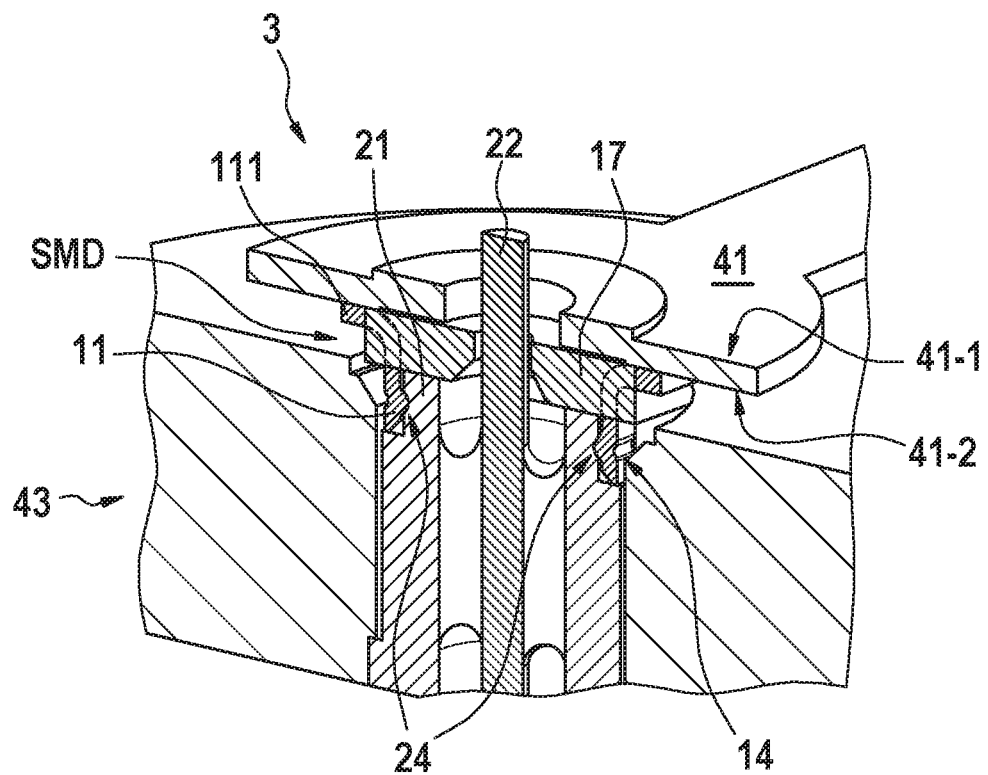
FIG. 10 shows a cross-sectional view of the second connector portion of FIG. 9 connected with a first connector portion.

FIG. 10 shows a cross-sectional view of the second (male) connector portion 2 of FIG. 9 coaxially connected with a part of a first connector portion 1. What has been stated above regarding the first connector portion 1 of FIGS. 1-5 also applies to the first connector portion 1 here. In particular, in FIG. 10, the first contact element 11 of the first connector portion 1 is force-fittingly and form-fittingly connected with the second contact element 21 of the second connector portion 2 by means of a spring connection or snap-in connection, as described above. Further, the contact pin 22 extends through bores provided in the insulation element 17 and the PCB 41. The contact pad 15 forming the pin receptacle 12 in FIGS. 1-5 is not shown in FIG. 10.

Figure 11:
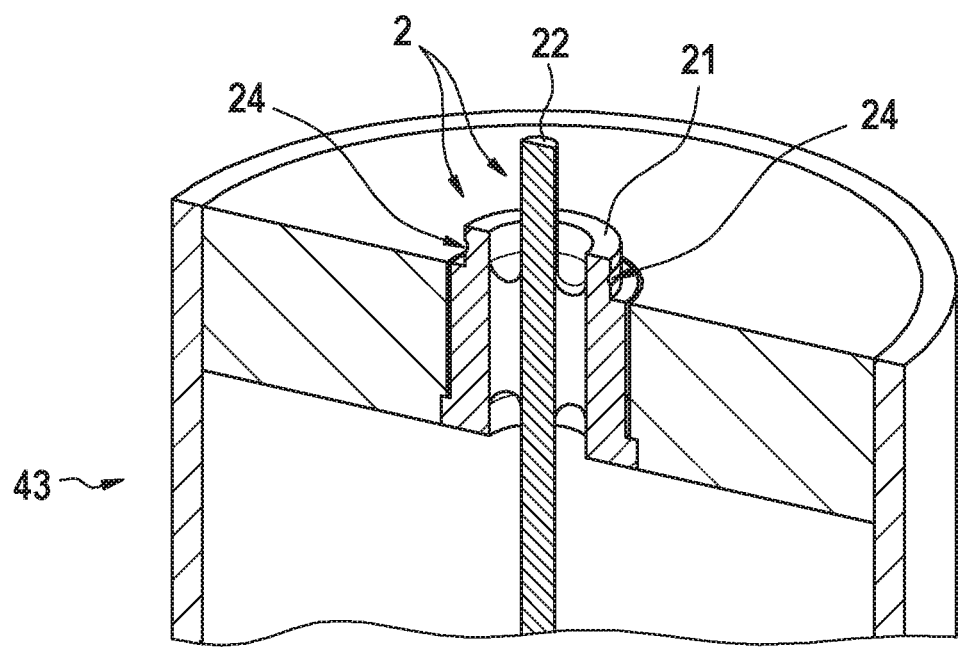
FIG. 11 shows a cross-sectional view of another version of a second connector portion.

FIG. 11 shows a cross-sectional view of another exemplary version of a second connector portion 2. Here the second contact element 21 is integrated with the housing of the feedthrough assembly 43, and axially protrudes from the surface of the housing of the feedthrough assembly 43, thereby defining a portion of the outer contour of the housing of the feedthrough assembly 43.

Figure 12:
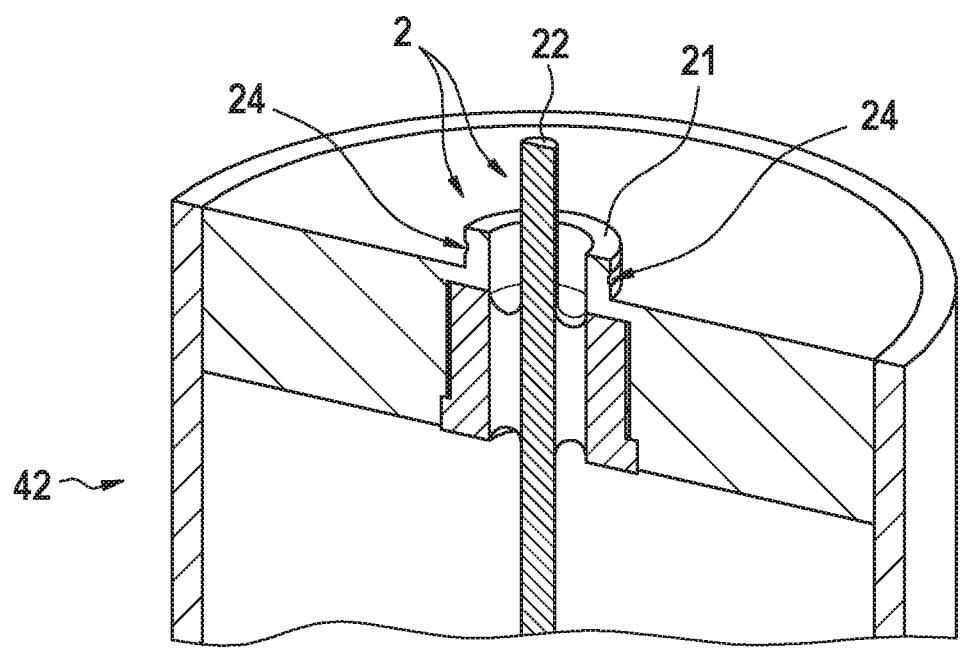
FIG. 12 shows a cross-sectional view of yet another version of second connector portion.

FIG. 12 shows a cross-sectional view of yet another exemplary version of the second connector portion 2. Here the second connector portion 2 is arranged on a battery 42, with the second contact element 21 being integrated into the housing of the battery 42 and axially protruding from a front surface of the housing. The arrangement is otherwise similar to that of FIG. 11.

Figure 13:
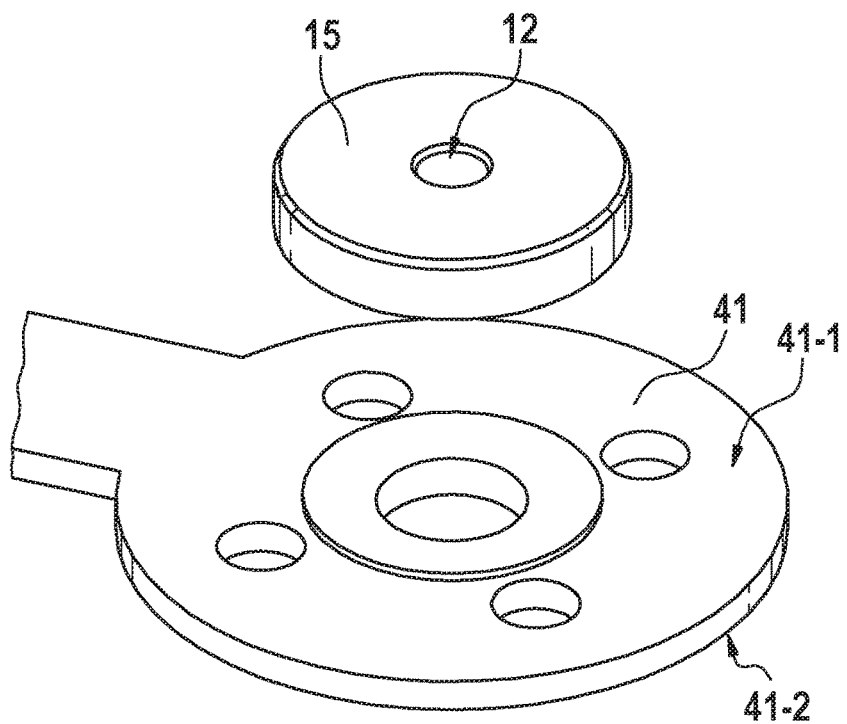
FIG. 13 shows a perspective view of a PCB and a contact pad forming a pin receptacle.

FIG. 13 shows a perspective view of a PCB 41 and a contact pad 15 forming a pin receptacle 12, wherein the contact pad 15 is not (yet) mounted on the front side 41-1 of the PCB 41. In this exemplary version, the PCB 41 includes four alignment bores that are arranged around a central bore that is provided to accept the connection pin 22 of the second connector portion 2 in the connected state of the connector arrangement 3.

Figure 14:
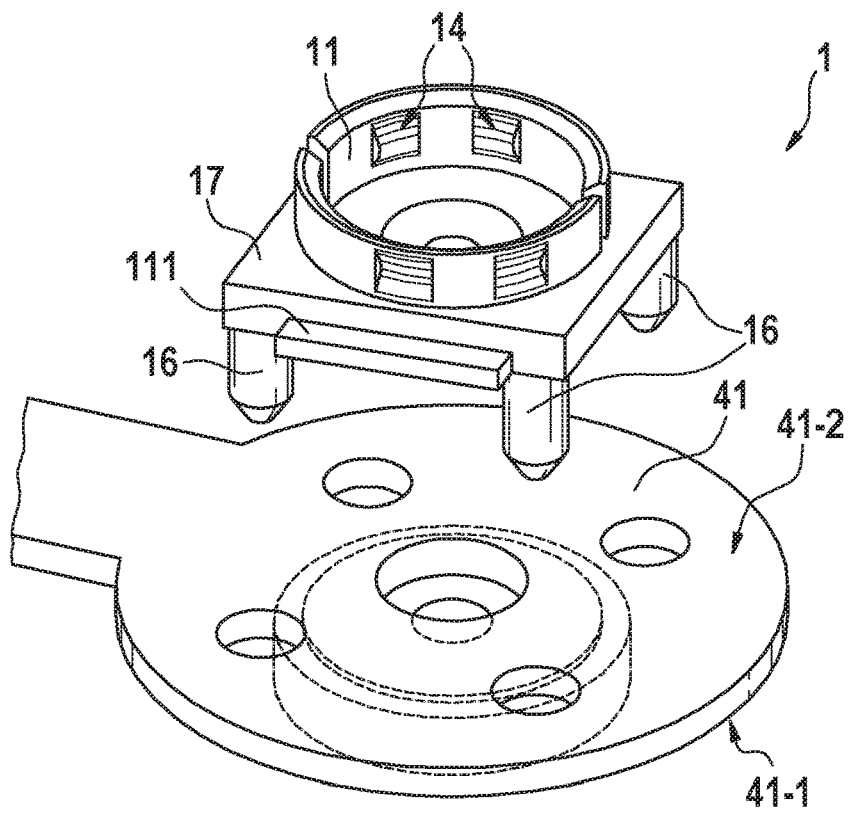
FIG. 14 shows the other side of the PCB of FIG. 13 and a first contact element arranged on an insulation element.
Figure 15:
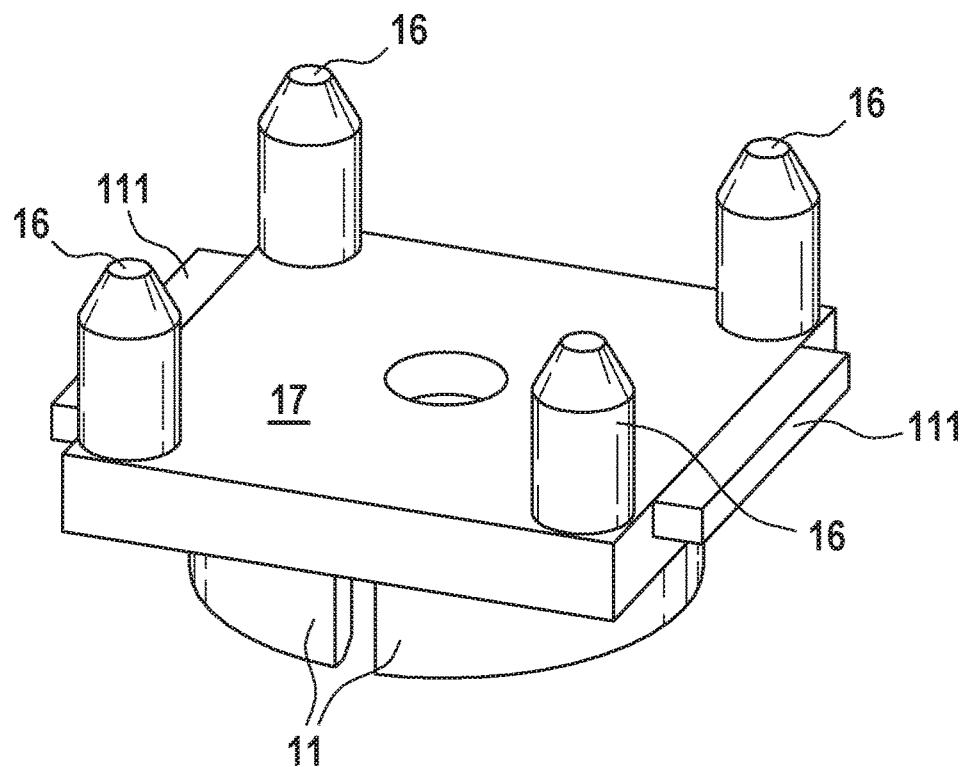
FIG. 15 shows a close-up perspective view of the insulation element and the first contact element of FIG. 14.

FIG. 14 shows the backside 41-2 of the PCB 41 of FIG. 13, as well as an SMD formed by a first contact element 11 provided on an insulation element 17. The insulation element 17 includes four guidance elements 16 which protrude from the four corners of the insulation element 17. FIG. 15 shows a close-up perspective view of the first contact element 11 and the insulation element 17, including the guidance elements 16.

Figure 16:
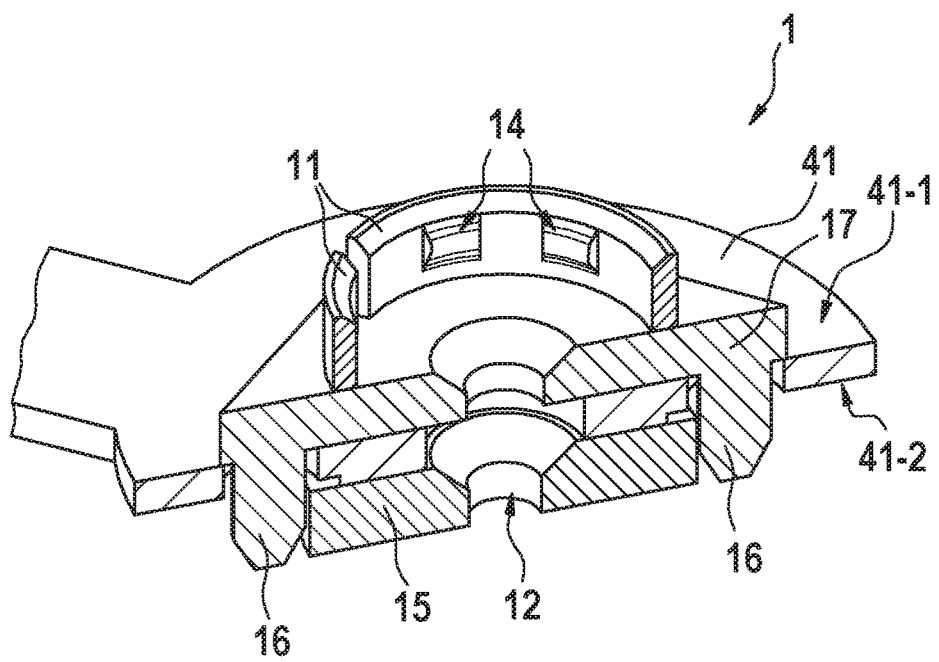
FIG. 16 shows a cross-sectional view of the PCB, the contact pad, and the insulation element with the first contact element in an assembled state.

FIG. 16 shows a cross-sectional view of the PCB 41, the contact pad 15, and the insulation element 17 of FIGS. 13-15 in an assembled state. In the assembled state, each of the insulation element 17 and the contact pad 15 are soldered to a respective side of the PCB 41, with the guidance elements 16 extending through the alignment bores provided in the PCB 41. Thus, the guidance elements 16 (in connection with the alignment bores provided in the PCB 41) are configured to axially align the contact element 11, the PCB 41, and the contact pad 15 that forms the pin receptacle 12, e.g., during the reflow soldering or other fixture processes which attach the insulation element 17 and the contact pad 15 to the PCB 41.

For example, during a reflow soldering process, when each of the contact pad 15 and the insulation element 17 "swim" in the solder for a short while before the solder then solidifies during cooling off, there is a risk that an axial offset between these contact components may arise. The inclined insertion surfaces 155, 177 may compensate for such offset by guiding the contact pin towards the hole (i.e., the pin receptacle 12) formed in the contact pad 15. To further minimize such position tolerances, the guidance elements 16 are provided on the insulation element 17 so as to ensure axial alignment and avoid unwanted displacement during the reflow process (i.e., while the solder is liquid).

For example, as illustrated in FIG. 16, the guidance elements 16 may laterally engage with a circumferential edge of the contact pad 15 so as to establish axial alignment. The guidance elements 16 extend through alignment bores provided in the PCB 41. In an alternative version (not shown), a portion of the PCB 41 may be smaller than the insulation element 17 such that the guidance elements 16 may laterally engage with a circumferential edge of said portion of the PCB 41 instead of extending through dedicated alignment bores provided in the PCB 41. In another alternative version (also not shown), the contact pad 15 may include dedicated alignment bores through which the guidance elements 16 may extend upon assembly of the first connector portion 1.

Figure 17:
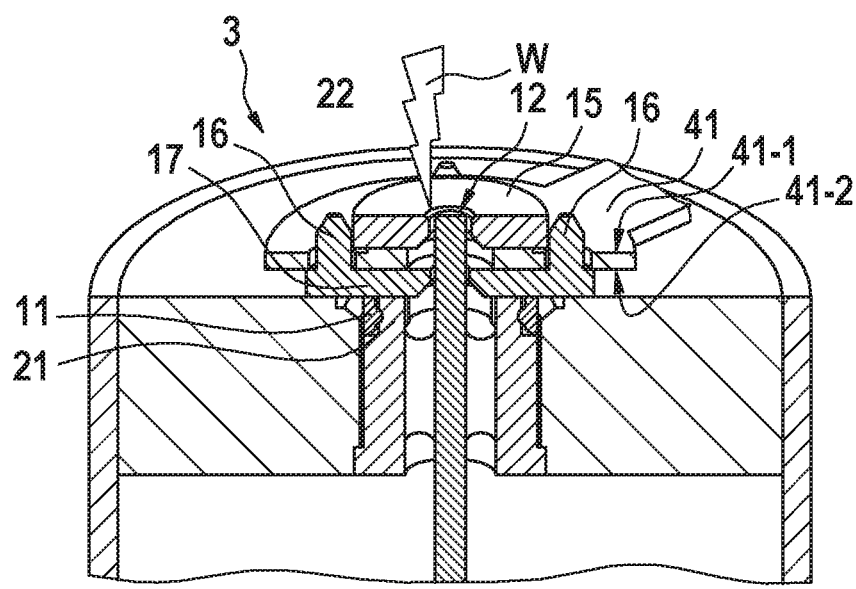
FIG. 17 shows a cross-sectional view of the first connector portion of FIG. 16 connected to a second connector portion of a battery.

FIG. 17 shows a cross-sectional view of the first connector portion 1 of FIG. 16, which is connected to a second connector portion 2 of a battery 42. As described above with reference to FIG. 3, in the mated condition, the contact pin 22 may be materially bonded with the pin receptacle 12, e.g., by means of a laser welding process W.

Figure 18:
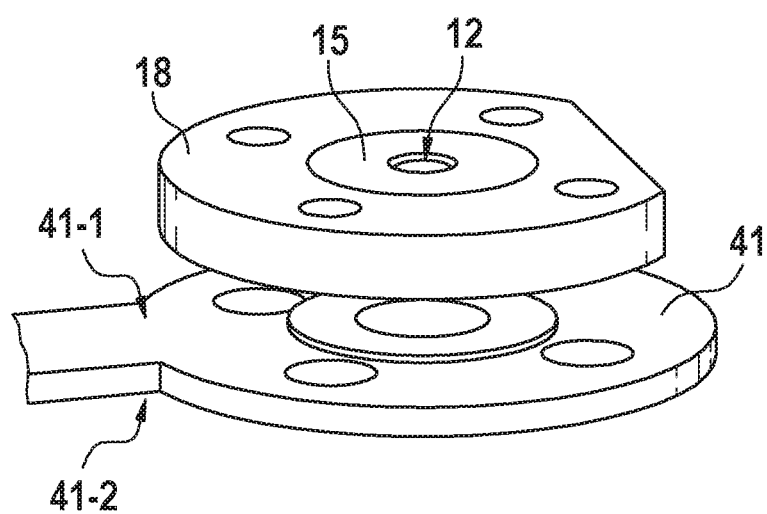
FIG. 18 shows a PCB and a contact pad forming a pin receptacle and having a plastic border.
Figure 19:
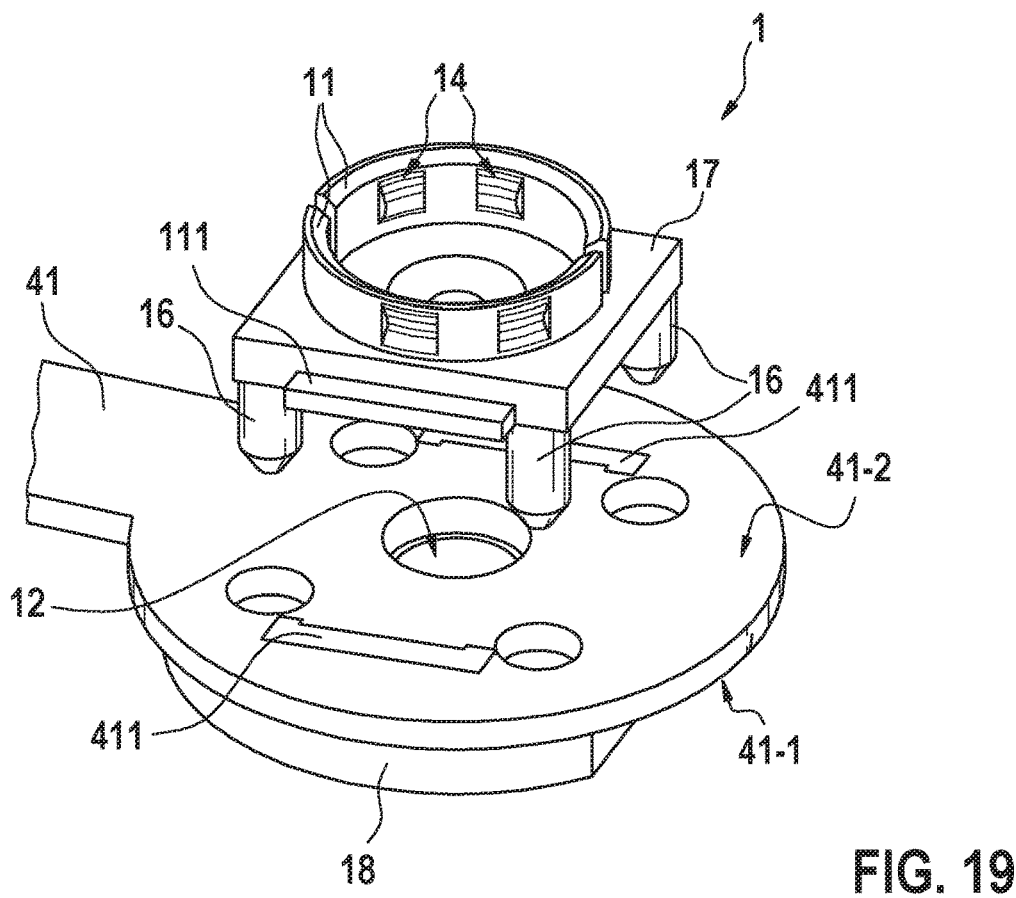
FIG. 19 shows the components of FIG. 18 and a first contact element arranged on an insulation element.

FIG. 18 shows another exemplary version of a PCB 41 and a contact pad 15 forming a pin receptacle 12. In this version, the contact pad 15 is surrounded by a ring-shaped plastic border 18, wherein the plastic border 18 includes four alignment bores matching the alignment bores of the PCB 41. FIG. 19 shows the components depicted in FIG. 18, and additionally a first contact element 11 provided on an insulation element 17. The insulation element 17 has four guidance elements 16, as described above in reference to FIGS. 14-17. In FIG. 19, bond pads 11 are configured to establish an electrical connection with the bond feet 111 when the SMD having the insulation element 17 and the first contact element 11 is fit to the second side 41-2 of the PCB 41.

Figure 20:
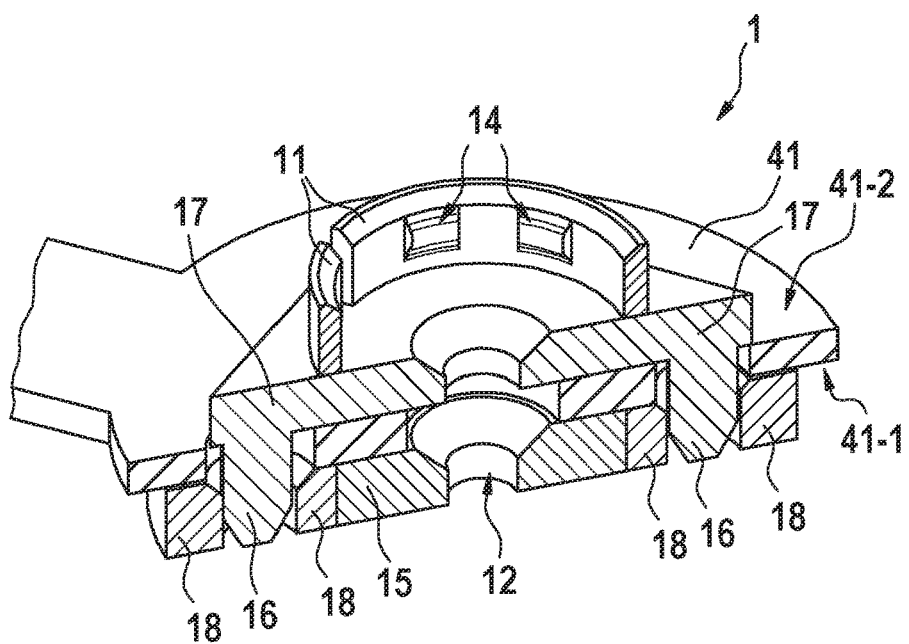
FIG. 20 shows the components of FIG. 19 is in an assembled state.

FIG. 20 shows the components of FIG. 19 is in an assembled state, wherein the guidance elements 16 extend into the alignment bores of the plastic border 18, thereby providing an exact concentric alignment of the central bores in the insulation element 17 and the contact pad 15. In an alternative version (not shown), the plastic border 18 of the contact pad 15 (instead of the insulation element 17) may be provided with protruding guidance elements, whereas the insulation 17 (instead of the plastic border 18) may have corresponding alignment bores.

Figure 21:
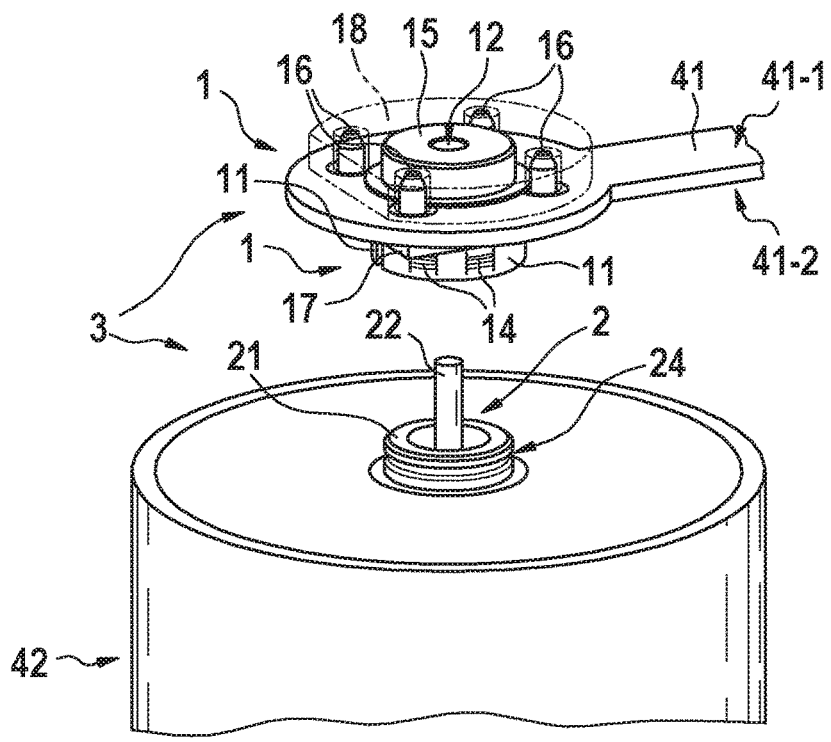
FIG. 21 shows a perspective view of the first connector portion of FIG. 20 and a battery having a second connector portion.
Figure 22:
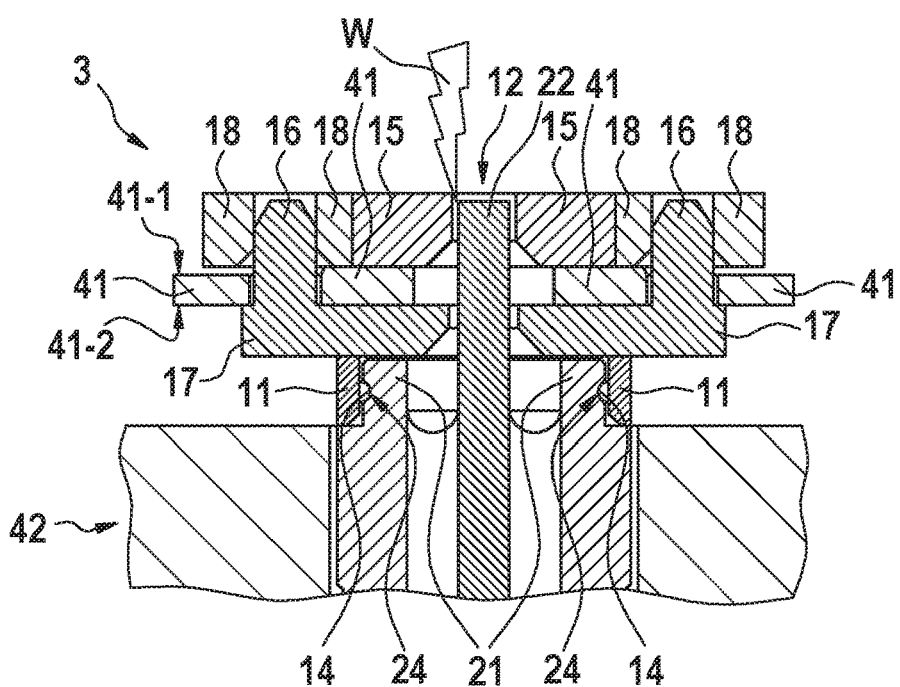
FIG. 22 shows a cross-sectional view of the connector arrangement of FIG. 21 in a connected state.

FIG. 21 shows a perspective view of the first connector portion 1 of FIG. 20 and a battery 42 having a second contact portion 2 as described above in connection with, e.g., FIG. 12. In FIG. 21, the connector assembly 3 is in a disconnected state. FIG. 22 shows a cross-sectional view of the connector arrangement 3 of FIG. 21 in the connected state, wherein the connector pin is metallurgically bonded with the contact pad 15 that forms the pin receptacle 12. The metallurgical bond may be created, e.g., by means of a laser welding process W.

Figure 23:
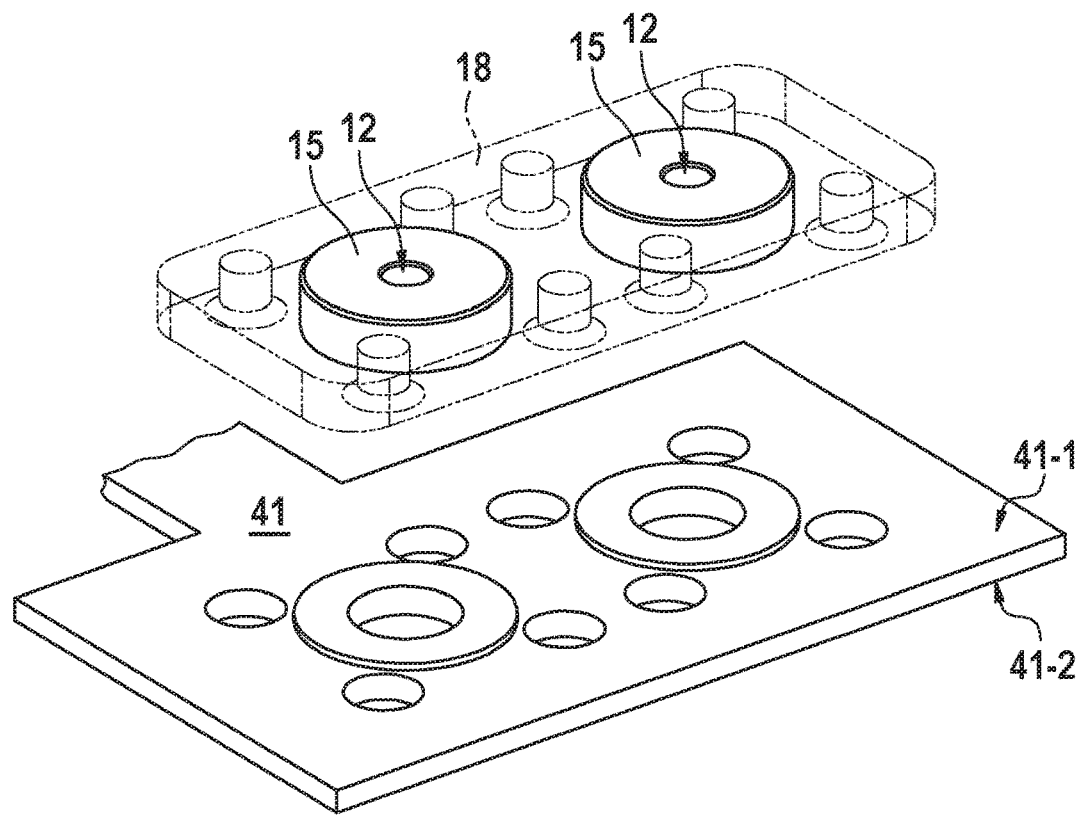
FIG. 23 shows a perspective view of a PCB and an array of two contact pads, each forming a respective pin receptacle and having a common plastic border.
Figure 24:
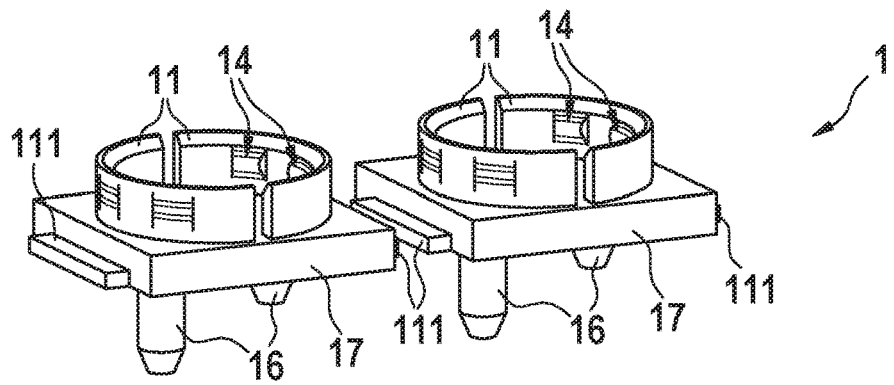
FIG. 24 shows the PCB and the contact pad array of FIG. 23 as well as two first contact elements arranged on respective insulation elements.
Figure 24:
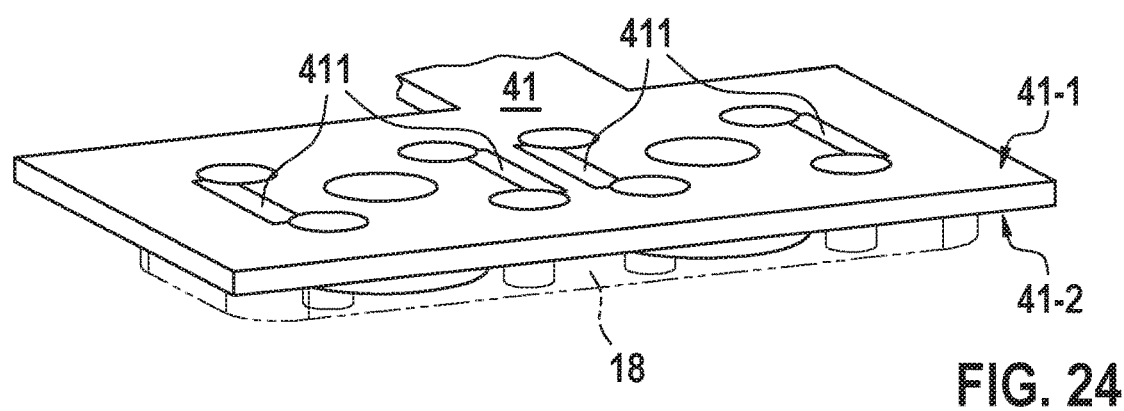
Figure 25:
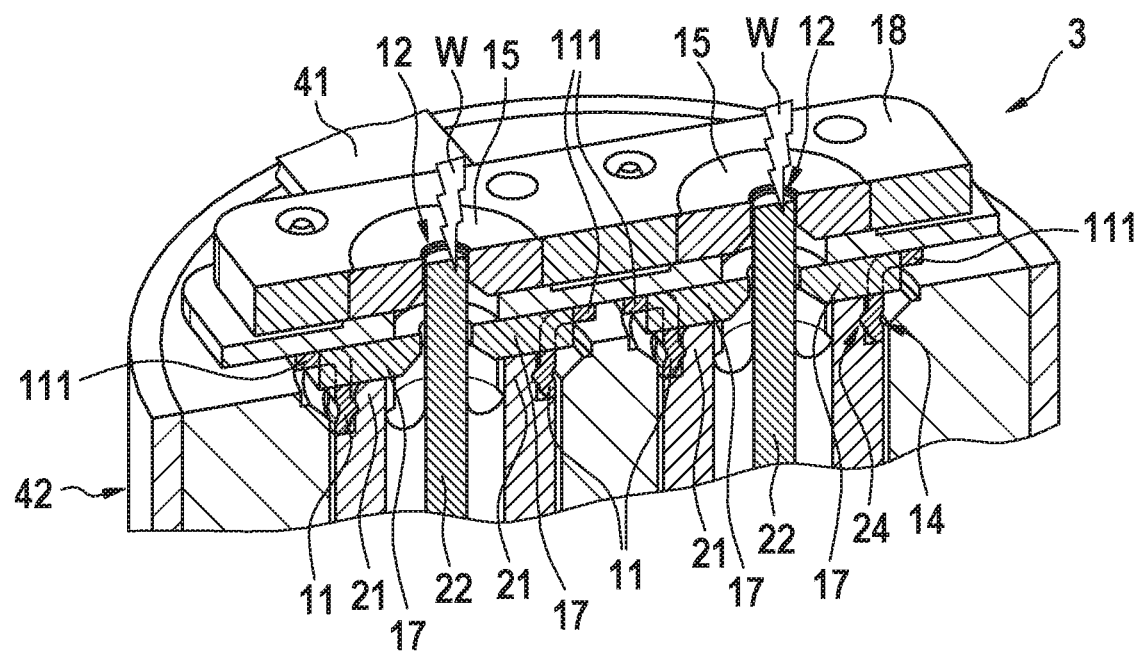
FIG. 25 shows a cross-sectional view of the first connector portion of FIG. 24 connected to a second connector portion of a battery.

FIG. 23 shows a perspective view of a PCB 41 and an array of two contact pads 15, each forming a respective pin receptacle 12. In this exemplary version, the two contact pads 15 are surrounded (and connected to each other) by a common plastic border 18. The PCB 41 includes a total of eight alignment bores. Correspondingly, eight alignment bores are also provided in the plastic border 18. FIG. 24 shows the PCB 41 and the contact pad array 15 of FIG. 23 as well as two first contact elements 11 that are arranged on respective insulation elements 17. FIG. 25 shows a cross-sectional view of the first connector portion 1 of FIG. 24 connected to a second connector portion 2 of a battery 42. Similar to what has been described above, also in this version, which uses an array of two pin receptacles 12 and two corresponding contact pins 22, each contact pin 22 may be welded to the respective contact pad 15 in the mated condition of the connector arrangement 3. For example, corresponding welding spots may be created by means of a laser welding process W.

Figure 26:
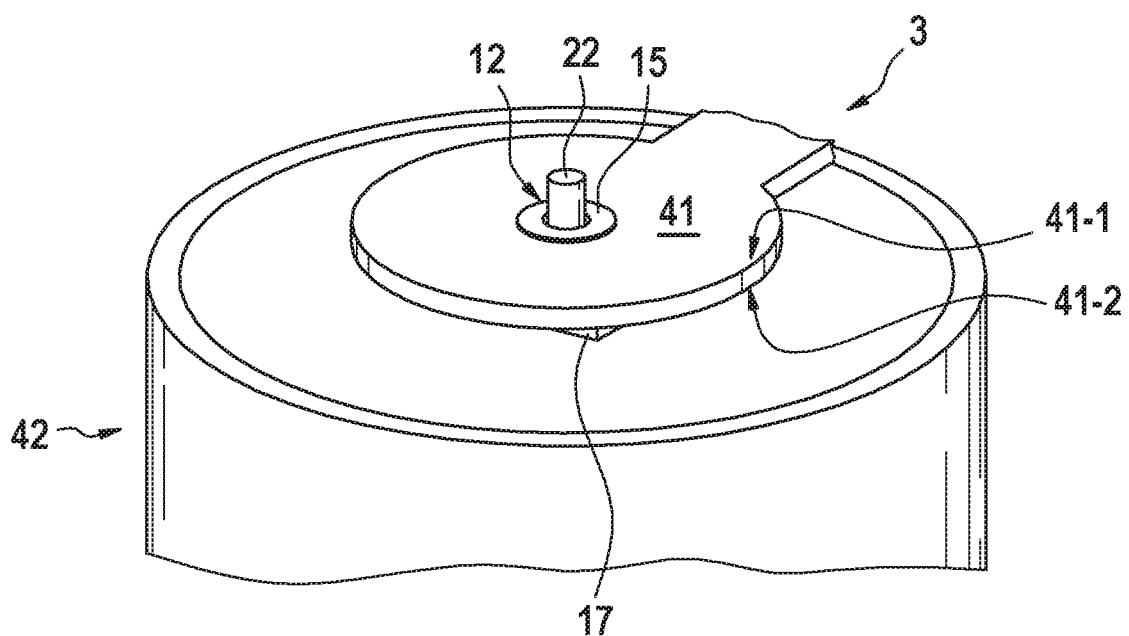
FIG. 26 shows a perspective view of a connector arrangement in the connected state.
Figure 27:
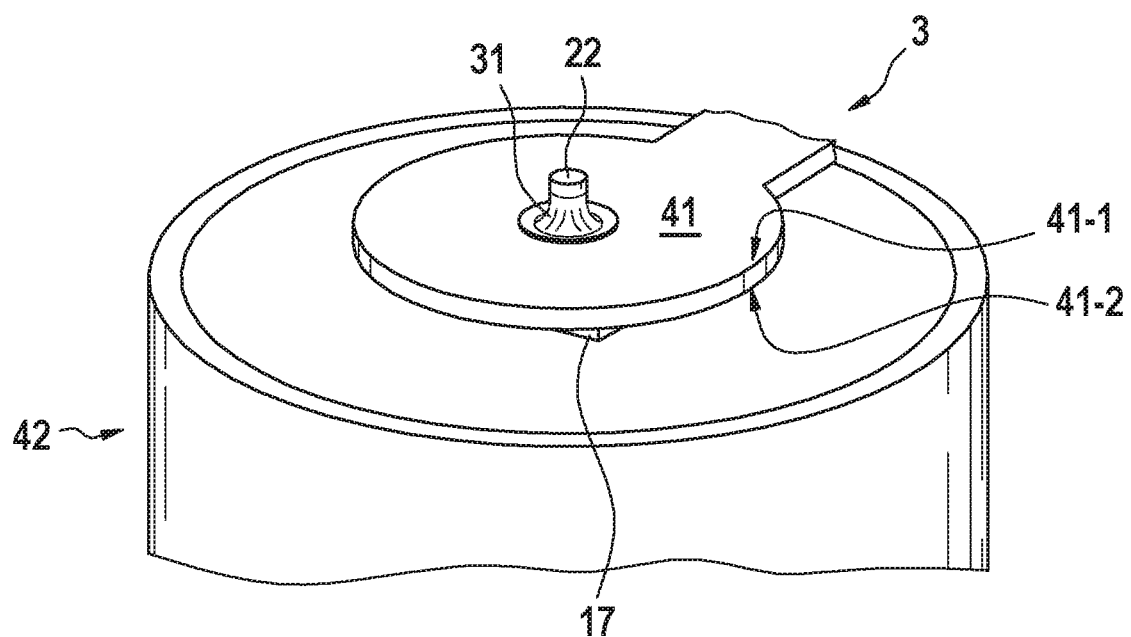
FIG. 27 shows the connector arrangement of FIG. 26, wherein the contact pin is soldered to the pin receptacle.
Figure 28:
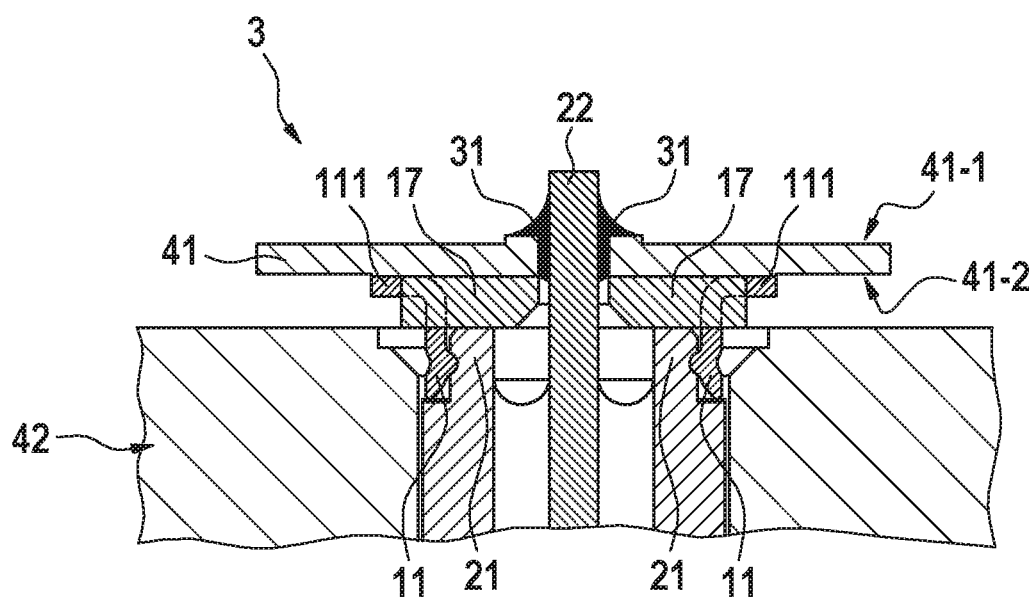
FIG. 28 shows a cross-sectional view of the connector arrangement of FIG. 27.

FIG. 26 shows a perspective view of yet another exemplary version of a connector arrangement 3 in the connected state. In this version, the contact pad 15 is arranged directly on the PCB 41 and has a ring-shaped solderable surface that surrounds the pin receptacle 12. In the connected state, a distal end of the contact pin 22 extends through the pin receptacle 12 and axially protrudes above the PCB 41 and the solderable surface of the contact pad 15. The contact pin 22 may be appropriately plated, e.g., with gold, palladium or ENIG, so as to better enable soldering. FIG. 27 shows the connector arrangement of FIG. 26, wherein the contact pin 22 is soldered to the pin receptacle 12 via soft solder 31. In other words, the material bond between the connector pin 22 and the pin receptacle 12 is created by means of a soft solder process. This is further illustrated in FIG. 28, which shows a cross-sectional view of the connector arrangement 3 of FIG. 27.

Figure 29:
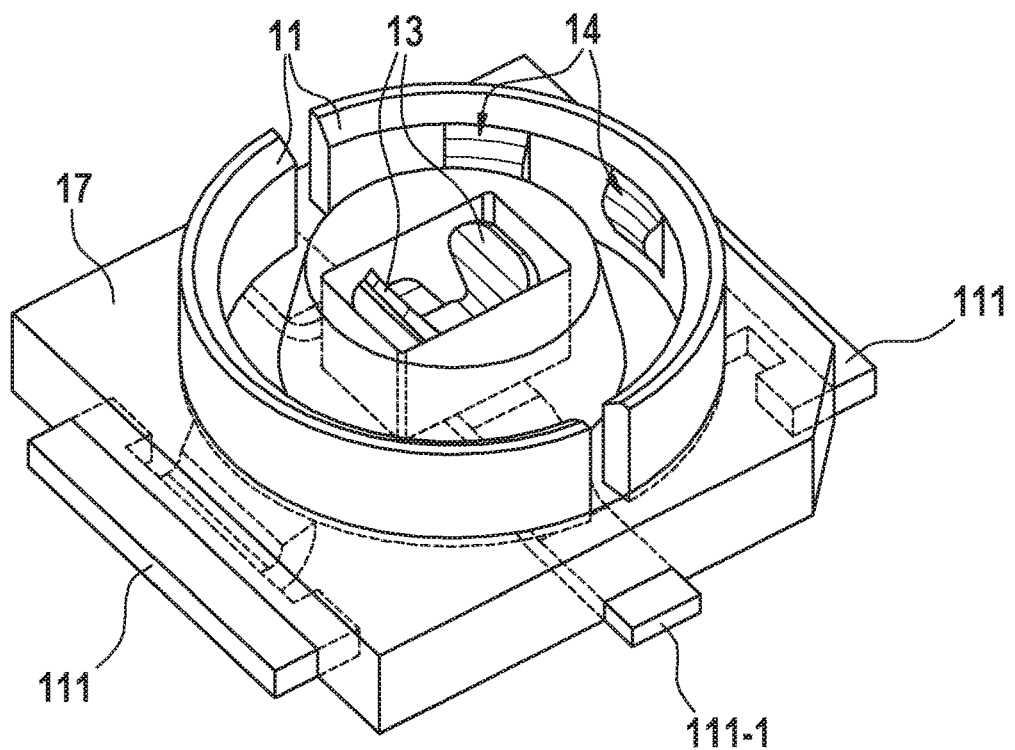
FIG. 29 shows another version of a first connector portion, wherein the pin receptacle is formed by a first spring element.

FIG. 29 shows another version of a first connector portion 1, wherein the pin receptacle 12 is defined within a first spring element 13 configured to clamp the distal end of the contact pin 22 in the connected state, thereby establishing a form-fitting and force-fitting connection between the pin receptacle 12 and the contact pin 22. The first spring element 13 may be connected to, or integrally formed with, one or more solderable bond feet 111-1. The material and/or plating of the first spring element 13 and/or of the bond feet 111-1 may be the same as the material and/or plating of the first contact element 11 (which may include phosphorous, bronze, nickel, gold or ENIG, as explained above).

Figure 30:
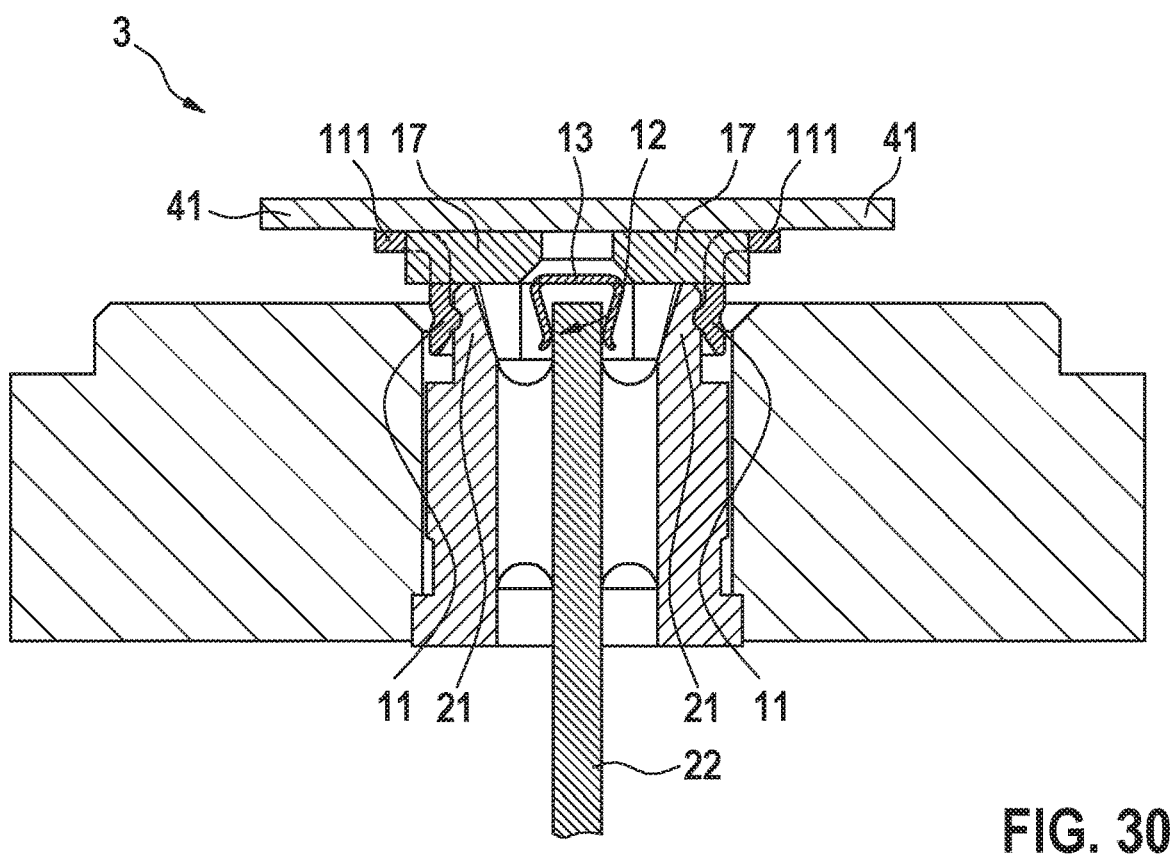
FIG. 30 shows a cross-sectional view of the first connector portion of FIG. 29 connected with a second connector portion.

FIG. 30 shows a cross-sectional view of the connector assembly 3 wherein the first connector portion 1 of FIG. 29 is connected with the second connector portion 2. In the connected state, the contact pin 22 is clamped inside the first spring element 13. In this version, the contact pin 22 does not extend through the PCB 41 in the connected state. The first contact element 11 and the second contact element 21 are connected by means of a spring connection or snap-in connection, as described above.

Figure 31:
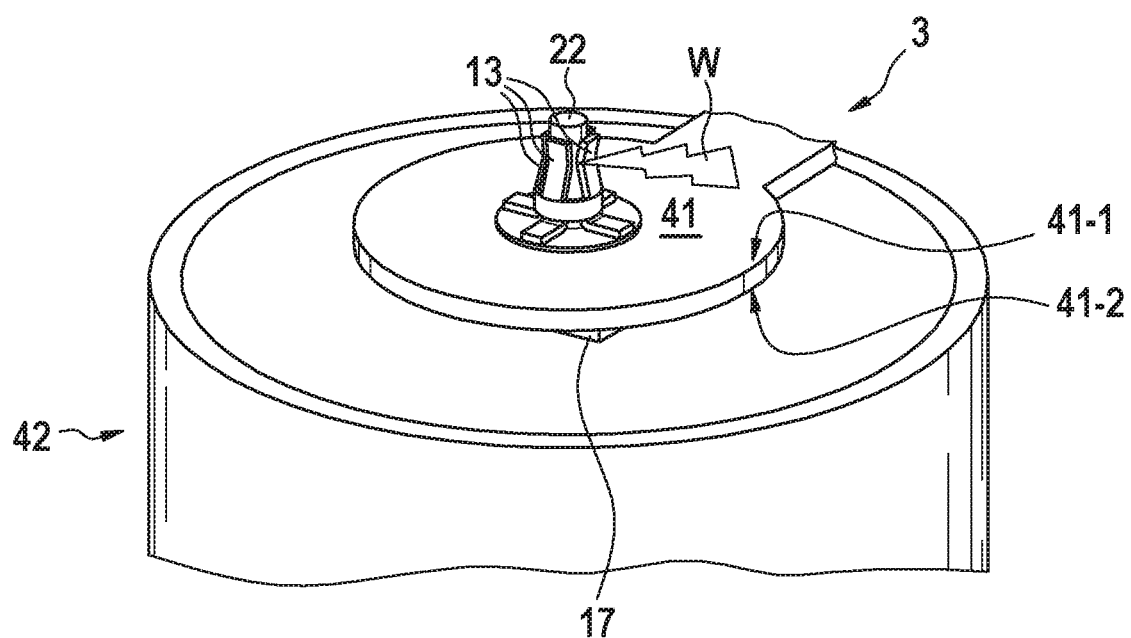
FIG. 31 shows yet another version of a connector assembly having a spring connection for securing the contact pin in the connected position.
Figure 32:
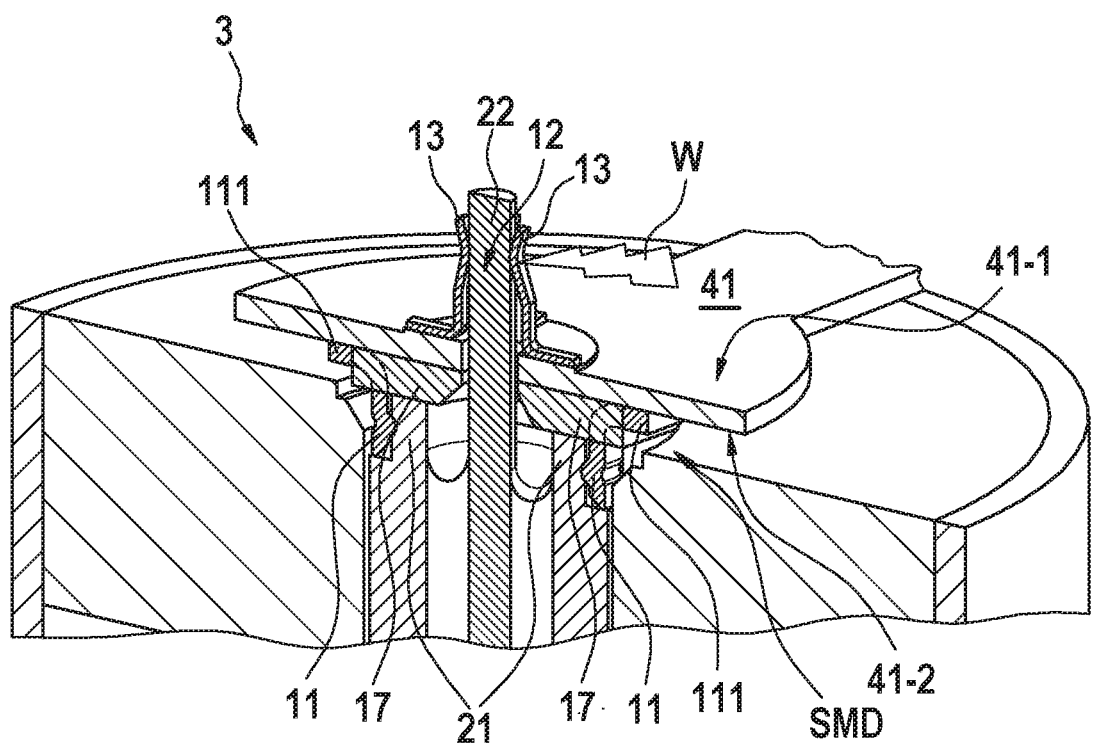
FIG. 32 shows a cross-sectional view of the connector assembly of FIG. 31.

FIG. 31 shows yet another version of a connector assembly 3 having a first spring connection 13 for securing the contact pin 22 in the connected position. In this exemplary version, the first spring connection 13 is provided on the contact pad 15, i.e., on the first side 41-1 of the PCB 41. In the connected state, the distal end of the contact pin 22 extends through the PCB and is clamped by and within the first spring element 13. Optionally, a metallurgical bond may be created between the first spring element 13 and the contact pin 22, e.g., by means of a laser welding process W. This version is further illustrated in FIG. 32, which shows a cross-sectional view of the connector assembly 3 of FIG. 31.

The versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A connector arrangement (3) for establishing a two-pole electric contact between components of an implantable medical device (4), the connector arrangement (3) including:
   A. a first connector portion (1) including a first contact element (11) and a pin receptacle (12), and
   B. a second connector portion (2) including a second contact element (21) and a contact pin (22),
   wherein:
   a. at least a part of the first connector portion (1) and/or at least a part of the second connector portion (2) is mounted on a printed circuit board (41),
   b. the pin receptacle (12) is situated on a first side (41-1) of the printed circuit board (41),
   c. the first contact element (11) is situated on an opposing second side (41-2) of the printed circuit board (41), and
   d. the connector arrangement (3) is configured to assume a connected state in which:
      (1) the first contact element (11) is in contact with the second contact element (21), and
      (2) the contact pin (22) is received in the pin receptacle (12).

2. The connector arrangement (3) of claim 1 wherein at least one of the first connector portion (1) and the second connector portion (2) defines at least a part of a surface-mount device (SMD) mounted on the printed circuit board (41).

3. The connector arrangement (3) of claim 1 wherein:
   a. the connector arrangement (3) is in the connected state, and
   b. the contact pin (22) is materially bonded with the pin receptacle (12).

4. The connector arrangement (3) of claim 3 wherein the contact pin (22) is bonded with the pin receptacle (12) by means of at least one of:
   a. a welded joint,
   b. a soldered joint, and
   c. a brazed joint.

5. The connector arrangement (3) of claim 1 wherein:
   a. the connector arrangement (3) is in the connected state, and
   b. the contact pin (22) is form-fittingly and/or force-fittingly connected to the pin receptacle (12).

6. The connector arrangement (3) of claim 1 wherein the first connector portion (1) includes a first spring element (13) configured to establish a form-fitting and/or force-fitting connection between the pin receptacle (12) and the contact pin (22) when the connector arrangement (3) is in the connected state.

7. The connector arrangement (3) of claim 1 wherein the first contact element (11) and the second contact element (21) are configured to be connected with each other in the connected state of the connector arrangement (3) by means of a spring connection and/or by means of a snap-in connection.

8. The connector arrangement (3) of claim 7 wherein:
   a. one of the first contact element (11) and the second contact element (21) includes a second spring element (14), and
   b. the other of the first contact element (11) and the second contact element (21) includes a groove (24),
   c. the second spring element (14) engages with the groove (24) in the connected state of the connector arrangement (3).

9. The connector arrangement (3) of claim 1 wherein at least one of the first contact element (11) and the second contact element (21) has an annular shape.

10. The connector arrangement (3) of claim 1 wherein each of the first contact element (11), the second contact element (21), the contact pin (22), and the pin receptacle (12) are coaxially situated when in the connected state of the connector arrangement (3).

11. A connector arrangement (3) for establishing a two-pole electric contact between components of an implantable medical device (4), the connector arrangement (3) including:
   A. a first connector portion (1) including a first contact element (11), a pin receptacle (12), a contact pad (15), and a guidance element (16) configured to align the first contact element (11) and the contact pad (15),
   B. a second connector portion (2) including a second contact element (21) and a contact pin (22),
   wherein:
   a. at least a part of the first connector portion (1) and/or at least a part of the second connector portion (2) is mounted on a printed circuit board (41),
   b. the connector arrangement (3) is configured to assume a connected state in which:
      (1) the first contact element (11) is in contact with the second contact element (21), and
      (2) the contact pin (22) is received in the pin receptacle (12).

12. The connector arrangement (3) of claim 1 further including an implantable medical device, wherein at least one of the first connector portion (1) and the second connector portion (2) is mounted on a printed circuit board (41) defining a portion of an electronics module of the implantable medical device (4).

13. The connector arrangement (3) of claim 12 wherein:
   a. the first connector portion (1) is mounted on the printed circuit board (41), and
   b. the second connector portion (2) is situated on a battery (42) or on a capacitor of the implantable medical device (4).

14. The connector arrangement (3) of claim 11 wherein:
   a. the pin receptacle (12) is situated on a first side (41-1) of the printed circuit board (41), and
   b. the first contact element (11) is situated on an opposing second side (41-2) of the printed circuit board (41).

15. The connector arrangement (3) of claim 11 wherein the first connector portion (1) includes a first spring element (13) configured to establish a form-fitting and/or force-fitting connection between the pin receptacle (12) and the contact pin (22) when the connector arrangement (3) is in the connected state.

16. The connector arrangement (3) of claim 11 wherein:
   a. one of the first contact element (11) and the second contact element (21) includes a second spring element (14), and
   b. the other of the first contact element (11) and the second contact element (21) includes a groove (24),
   c. the second spring element (14) engages with the groove (24) in the connected state of the connector arrangement (3).

17. The connector arrangement (3) of claim 11 wherein at least one of the first contact element (11) and the second contact element (21) has an annular shape.

18. The connector arrangement (3) of claim 11 wherein each of the first contact element (11), the second contact element (21), the contact pin (22), and the pin receptacle (12) are coaxially situated when in the connected state of the connector arrangement (3).

19. The connector arrangement (3) of claim 11 further including an implantable medical device, wherein at least one of the first connector portion (1) and the second connector portion (2) is mounted on a printed circuit board (41) defining a portion of an electronics module of the implantable medical device (4).

20. A connector arrangement (3) for establishing a two-pole electric contact between components of an implantable medical device (4), the connector arrangement (3) including:
   a. a printed circuit board (41) having a bore defined therein;
   b. a first connector portion (1) including:
      (1) a conductive contact pad (15) situated adjacent a first side (41-1) of the printed circuit board (41), the contact pad (15) having a pin receptacle (12) thereon, the pin receptacle (12) being aligned with the bore,
      (2) a conductive first contact element (11) situated adjacent an opposing second side (41-2) of the printed circuit board (41), the first contact element (11) extending along a path orbiting at least a major portion of the circumference of the bore;

c. a second connector portion (2) including:
  (1) an elongated conductive contact pin (22):
    (a) extending through the bore and into the pin receptacle (12), and
    (b) being electrically connected to the contact pad (15);
  (2) a conductive second contact element (21):
    (a) spaced from the circumference of the contact pin (22),
    (b) extending along a path orbiting at least a major portion of the circumference of the contact pin (22), and
    (c) being electrically connected to the first contact element (11).

* * * * *